United States Patent
Petitjean

(10) Patent No.: US 11,798,163 B2
(45) Date of Patent: *Oct. 24, 2023

(54) SYSTEMS AND METHODS FOR QUANTITATIVE PHENOTYPING OF FIBROSIS

(71) Applicant: PharmaNest LLC, Princeton, NJ (US)

(72) Inventor: Mathieu Maurice Petitjean, Princeton, NJ (US)

(73) Assignee: PHARMANEST LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,332

(22) Filed: Jul. 21, 2022

(65) Prior Publication Data

US 2023/0019599 A1    Jan. 19, 2023

Related U.S. Application Data

(63) Continuation of application No. 16/851,881, filed on Apr. 17, 2020, now Pat. No. 11,430,112.

(Continued)

(51) Int. Cl.
*G06V 10/80* (2022.01)
*G06T 7/00* (2017.01)
*G06V 20/69* (2022.01)

(52) U.S. Cl.
CPC .......... *G06T 7/0012* (2013.01); *G06V 10/806* (2022.01); *G06V 10/809* (2022.01);
(Continued)

(58) Field of Classification Search
CPC .............. A61B 2576/00; A61B 5/4244; G01N 2333/78; G01N 33/4833; G06F 18/253;
(Continued)

(56) References Cited

U.S. PATENT DOCUMENTS 7,461,048 B2    12/2008    Teverovskiy et al.
7,761,240 B2    7/2010    Said et al.
(Continued)

FOREIGN PATENT DOCUMENTS

WO    WO-2014/109708 A1    7/2014

OTHER PUBLICATIONS

Sun, Y., et al, "Quantitative assessment of liver fibrosis (qFibrosis) reveals precise outcomes in Ishak 'stable' patients on anti-HBV therapy", Scientific Reports, vol. 8, No. 1, 11 pages, Feb. 14, 2018.

(Continued)

*Primary Examiner* — Tsung Yin Tsai
(74) *Attorney, Agent, or Firm* — White & Case LLP

(57) ABSTRACT

Systems and methods are provided for computer aided phenotyping of fibrosis-related conditions. A digital image indicates presence of collagens in a biological tissue sample. The image is processed to quantify parameters, each parameter describing a feature of the collagens that is expected to be different for different phenotypes of fibrosis. At least some features are tissue level features that describe macroscopic characteristics of the collagens, morphometric level features that describe morphometric characteristics of the collagens, and texture level features that describe an organization of the collagens. At least some of the plurality of parameters are statistics associated with histograms corresponding to distributions of the associated parameters across at least some of the digital image. At least some of the plurality of parameters are combined to obtain one or more composite scores that quantify a phenotype of fibrosis for the biological tissue sample.

27 Claims, 20 Drawing Sheets

Related U.S. Application Data

(60) Provisional application No. 62/852,745, filed on May 24, 2019.

(52) U.S. Cl.
CPC .......... *G06V 20/695* (2022.01); *G06V 20/698* (2022.01); *G06T 2207/10056* (2013.01); *G06T 2207/30024* (2013.01)

(58) Field of Classification Search
CPC ......... G06F 18/254; G06T 2207/10056; G06T 2207/30024; G06T 2207/30056; G06T 7/0012; G06T 7/41; G06T 7/62; G06V 10/806; G06V 10/809; G06V 20/695; G06V 20/698
See application file for complete search history.

(56) References Cited

U.S. PATENT DOCUMENTS

| | | | |
|---|---|---|---|
| 8,094,915 B2 | 1/2012 | Dioguardi et al. | |
| 9,146,680 B2* | 9/2015 | Kulkarni | G06F 3/0656 |
| 9,710,908 B2 | 7/2017 | Yu et al. | |
| 10,229,488 B2 | 3/2019 | Yu et al. | |
| 10,766,860 B2* | 9/2020 | Rowbottom | C07D 213/56 |
| 11,120,888 B2* | 9/2021 | Korn | G16B 40/00 |
| 2002/0191823 A1* | 12/2002 | Wehrli | A61B 5/7264 |
| | | | 600/407 |
| 2005/0261180 A1* | 11/2005 | Pilon | A61K 38/1709 |
| | | | 514/1.5 |
| 2006/0064248 A1* | 3/2006 | Saidi | G06V 20/695 |
| | | | 382/128 |
| 2013/0030305 A1 | 1/2013 | Yu et al. | |
| 2015/0039816 A1* | 2/2015 | Kulkarni | G06F 3/061 |
| | | | 711/103 |
| 2015/0339816 A1 | 11/2015 | Yu et al. | |
| 2016/0200820 A1* | 7/2016 | Marshall | A61P 17/00 |
| | | | 424/139.1 |
| 2018/0046750 A1* | 2/2018 | Korn | G16B 5/00 |
| 2018/0057458 A1* | 3/2018 | Rowbottom | C07D 213/55 |
| 2018/0075600 A1 | 3/2018 | Cales et al. | |
| 2019/0133452 A1* | 5/2019 | Sanchez | A61B 5/1079 |
| 2019/0244347 A1 | 8/2019 | Buckler et al. | |
| 2021/0043331 A1* | 2/2021 | Ozcan | G06V 10/82 |

OTHER PUBLICATIONS

Xu, S., et al, "qFibrosis: A fully-quantitative innovative method incorporating histological features to facilitate accurate fibrosis scoring in animal model and chronic hepatitis B patients", Journal of Hepatology, Elsevier, Amsterdam, NL, vol. 61, No. 2, pp. 260-269, Feb. 26, 2014.

Xu, S., et al, "Supplementary data for qFibrosis: A fully-quantitative innovative method incorporating histological features to facilitate accurate fibrosis scoring in animal model and chronic hepatitis B patients", Journal of Hepatology, Feb. 26, 2014, pp. 1-29.

Yu, Y., et al, "Deep learning enables automated scoring of liver fibrosis stages", Scientific Reports, vol. 8, No. 1, 10 pages, Oct. 30, 2018.

Calès, Paul, et al, "Automated morphometry provides accurate and reproducible virtual staging of liver fibrosis in chronic hepatitis C," Journal of Pathology Informatics, vol. 6(1): p. 20 (total pp. 19) (2015).

EP First Examination Report (EP20729254.1) dated Jul. 25, 2023 (8 pages).

* cited by examiner

Tissue Level Parameters

F0

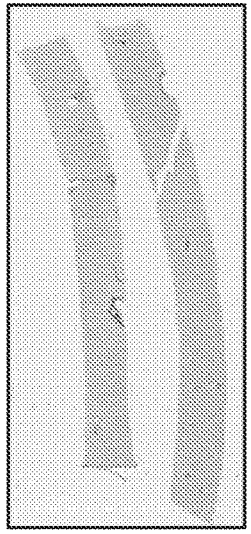

| Parameter | Value |
|---|---|
| Object Normalized Count | 59.43/mm² |
| Skeleton Nodes Normalized Count | 109.2/mm² |
| Collagen Reticulation Index | 1.41 |
| Total Collagen Area Ratio | 0.8% |
| Fine Collagen Area Ratio | 0.4% |

F2

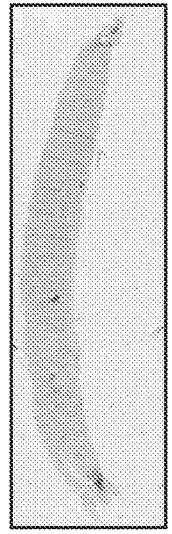

| Parameter | Value |
|---|---|
| Object Normalized Count | 203.8/mm² |
| Skeleton Nodes Normalized Count | 607.4/mm² |
| Collagen Reticulation Index | 1.6 |
| Total Collagen Area Ratio | 3.3% |
| Fine Collagen Area Ratio | 1.18% |

F4

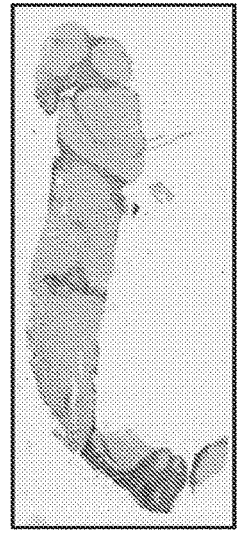

| Parameter | Value |
|---|---|
| Object Normalized Count | 439.2/mm² |
| Skeleton Nodes Normalized Count | 3656/mm² |
| Collagen Reticulation Index | 1.72 |
| Total Collagen Area Ratio | 20.1% |
| Fine Collagen Area Ratio | 2.28% |

This is also data from the Calibration Set

FIG. 3

Exemplary Tissue Level Parameters And Selection for a Fibrosis Severity Score

| Parameter | Fibrosis stage 0 | Fibrosis stage 2 | Fibrosis stage 4 | Selected |
|---|---|---|---|---|
| Fiber Normalized Count | 59.43 | 203.78 | 439.14 | 0 |
| Fine Collagen Normalized Count | 58.66 | 198.61 | 431.68 | 0 |
| Assembled Collagen Normalized Count | 0.76 | 5.17 | 7.46 | 0 |
| Skeleton Nodes Normalized Count | 109.19 | 607.44 | 3656.51 | 0 |
| Skeleton Branch Normalized Count | 236.39 | 1147.26 | 5321.95 | 1 |
| Collagen Reticulation Index | 1.41 | 1.60 | 1.72 | 0 |
| Collagen Structure Index | 3.46 | 5.68 | 14.59 | 0 |
| Total Collagen Area Ratio (%) | 0.80 | 3.30 | 20.10 | 1 |
| SQRT(Total Collagen Area Ratio %) | 0.89 | 1.83 | 4.48 | 1 |
| Fine Collagen Area Ratio (%) | 0.40 | 1.18 | 2.83 | 0 |
| SQRT(Fine Collagen Area Ratio %) | 0.64 | 1.09 | 1.68 | 0 |
| Assembled Collagen Area Ratio (%) | 0.39 | 2.16 | 17.26 | 1 |
| SQRT(Assembled Collagen Area Ratio %) | 0.63 | 1.47 | 4.16 | 0 |
| Total Collagen Density Area Ratio (%) | 0.14 | 0.49 | 3.56 | 1 |
| Assembled/Fine CAR Ratio | 0.92 | 1.78 | 6.10 | 1 |

FIG. 4

Morphometric | Length
F0
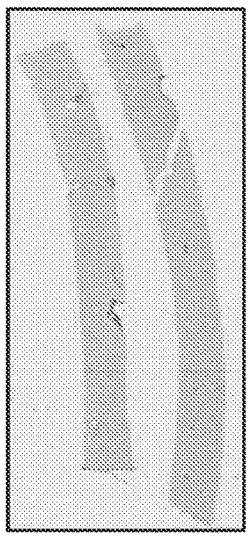
F2
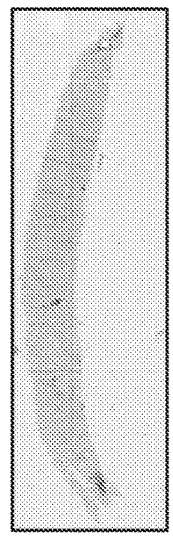
F4
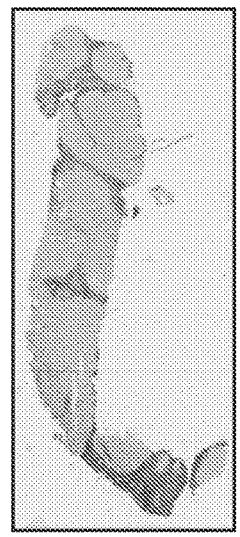
F0-Length
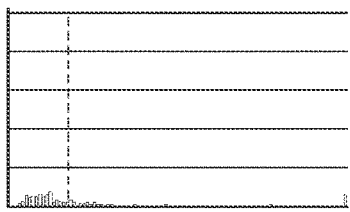
F2-Length
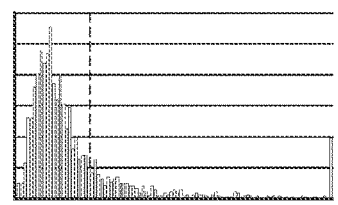
F4-Length
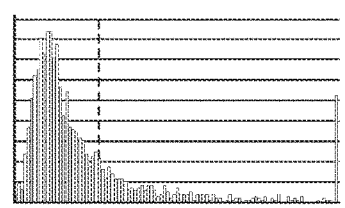
| Length | Value |
|---|---|
| Short | 30.9/mm$^2$ |
| Long | 31.8/mm$^2$ |
| Mean | 63.2px |
| Median | 31.0px |
| Std Dev | 123.3px |
| Skewness | 6.6 |
| Kurtosis | 55.0 |
| Length | Value |
|---|---|
| Short | 101.2/mm$^2$ |
| Long | 94.5/mm$^2$ |
| Mean | 49.31px |
| Median | 30.0px |
| Std Dev | 104.9px |
| Skewness | 14.3 |
| Kurtosis | 271.11 |
| Length | Value |
|---|---|
| Short | 185.4/mm$^2$ |
| Long | 197.3/mm$^2$ |
| Mean | 61.1px |
| Median | 31.00px |
| Std Dev | 183.85px |
| Skewness | 15.78 |
| Kurtosis | 290.71 |
This is also data from the Calibration Set
FIG. 5

700

Exemplary Morphometric Level Parameters and Selection for a Fibrosis Severity Score

| Parameter | Fibrosis Stage | | | Selected |
|---|---|---|---|---|
| | 0 | 2 | 4 | |
| Normalized Count of Short of Length for All - Collagen Phenotypes | 29.52 | 100.73 | 5.19 | 0 |
| Normalized Count of Long of Length for All - Collagen Phenotypes | 28.73 | 92.74 | 433.96 | 1 |
| Mean of Length for All - Collagen Phenotypes | 52.89 | 51.04 | 57.08 | 1 |
| Median of Length for All - Collagen Phenotypes | 30.00 | 30.00 | 31.00 | 0 |
| Std of Length for All - Collagen Phenotypes | 81.80 | 109.86 | 172.60 | 0 |
| Skew of Length for All - Collagen Phenotypes | 5.85 | 13.43 | 14.98 | 0 |
| Kurtosis of Length for All - Collagen Phenotypes | 41.62 | 239.93 | 256.70 | 0 |
| Normalized Count of Short of Total Skeleton Length for All - Collagen Phenotypes | 36.30 | 120.12 | 249.41 | 0 |
| Normalized Count of Long of Total Skeleton Length for All - Collagen Phenotypes | 21.94 | 73.35 | 189.73 | 1 |
| Mean of Total Skeleton Length for All - Collagen Phenotypes | 74.95 | 91.84 | 226.14 | 0 |
| Median of Total Skeleton Length for All - Collagen Phenotypes | 24.00 | 24.00 | 26.00 | 1 |
| Std of Total Skeleton Length for All - Collagen Phenotypes | 302.94 | 572.40 | 3052.70 | 0 |
| Skew of Total Skeleton Length for All - Collagen Phenotypes | 10.59 | 19.54 | 21.81 | 1 |
| Kurtosis of Total Skeleton Length for All - Collagen Phenotypes | 122.08 | 442.61 | 518.90 | 0 |
| Normalized Count of Thin of Width for All - Collagen Phenotypes | 11.36 | 33.53 | 0.65 | 1 |
| Normalized Count of Thick of Width for All - Collagen Phenotypes | 46.88 | 159.94 | 438.50 | 1 |
| Mean of Width for All - Collagen Phenotypes | 9.42 | 9.60 | 10.27 | 1 |
| Median of Width for All - Collagen Phenotypes | 7.65 | 8.00 | 8.49 | 1 |
| Std of Width for All - Collagen Phenotypes | 7.63 | 7.21 | 15.68 | 1 |
| Skew of Width for All - Collagen Phenotypes | 5.37 | 4.66 | 17.51 | 1 |
| Kurtosis of Width for All - Collagen Phenotypes | 42.51 | 35.93 | 391.32 | 1 |
| Normalized Count of Short of Perimeter for All - Collagen Phenotypes | 21.94 | 73.35 | 157.63 | 0 |
| Normalized Count of Long of Perimeter for All - Collagen Phenotypes | 36.30 | 120.12 | 281.52 | 1 |
| Mean of Perimeter for All - Collagen Phenotypes | 161.24 | 191.95 | 345.52 | 1 |
| Median of Perimeter for All - Collagen Phenotypes | 71.01 | 71.11 | 75.01 | 1 |
| Std of Perimeter for All - Collagen Phenotypes | 468.28 | 914.86 | 3575.71 | 0 |
| Skew of Perimeter for All - Collagen Phenotypes | 10.03 | 18.31 | 19.60 | 0 |
| Kurtosis of Perimeter for All - Collagen Phenotypes | 113.08 | 396.27 | 408.79 | 1 |
| Normalized Count of Small of Area for All - Collagen Phenotypes | 28.5 | 96.28 | 159.7 | 0 |
| Normalized Count of Large of Area for All - Collagen Phenotypes | 29.99 | 97.19 | 279.57 | 1 |
| Mean of Area for All - Collagen Phenotypes | 896.62 | 1000.64 | 3008.77 | 0 |
| Median of Area for All - Collagen Phenotypes | 208.00 | 201.00 | 218.00 | 1 |
| Std of Area for All - Collagen Phenotypes | 4464.35 | 7636.96 | 47493.66 | 1 |
| Skew of Area for All - Collagen Phenotypes | 10.33 | 22.17 | 25.00 | 0 |
| Kurtosis of Area for All - Collagen Phenotypes | 112.28 | 567.50 | 697.86 | 0 |

FIG. 7

Exemplary Texture Level Parameters and Selection for a Fibrosis Severity Score

| Parameter | Fibrosis Stage 0 | Fibrosis Stage 2 | Fibrosis Stage 4 | Selected |
|---|---|---|---|---|
| Normalized Count of Homogenous of Homogeneity for All - Fibrosis Texture | 10.89 | 66.54 | 10.70 | 0 |
| Normalized Count of Organized of Homogeneity for All - Fibrosis Texture | 337.31 | 331.01 | 474.82 | 0 |
| Mean of Homogeneity for All - Fibrosis Texture | 0.94 | 0.81 | 0.69 | -1 |
| Median of Homogeneity for All - Fibrosis Texture | 0.97 | 0.85 | 0.78 | -1 |
| Std of Homogeneity for All - Fibrosis Texture | 0.08 | 0.12 | 0.23 | 5 |
| Skew of Homogeneity for All - Fibrosis Texture | -4.16 | -2.39 | -0.89 | 0 |
| Kurtosis of Homogeneity for All - Fibrosis Texture | 23.11 | 7.45 | -0.59 | -1 |
| Normalized Count of Irregular of Correlation for All - Fibrosis Texture | 301.64 | 300.10 | 0.00 | -1 |
| Normalized Count of Patterned of Correlation for All - Fibrosis Texture | 46.56 | 97.46 | 485.52 | 1 |
| Mean of Correlation for All - Fibrosis Texture | 0.74 | 0.81 | 0.87 | 1 |
| Median of Correlation for All - Fibrosis Texture | 0.75 | 0.81 | 0.90 | 3 |
| Std of Correlation for All - Fibrosis Texture | 0.16 | 0.10 | 0.10 | 0 |
| Skew of Correlation for All - Fibrosis Texture | -0.95 | -0.15 | -0.76 | 0 |
| Kurtosis of Correlation for All - Fibrosis Texture | -1.85 | -0.86 | -0.47 | 0 |
| Normalized Count of Uniform of Inertia for All - Fibrosis Texture | 336.52 | 371.88 | 485.52 | 1 |
| Normalized Count of Contrasted of Inertia for All - Fibrosis Texture | 11.68 | 25.67 | 0.00 | 1 |
| Mean of Inertia for All - Fibrosis Texture | 4.12 | 8.74 | 34.61 | 5 |
| Median of Inertia for All - Fibrosis Texture | 0.00 | 2.00 | 6.00 | 0 |
| Std of Inertia for All - Fibrosis Texture | 17.42 | 25.16 | 54.61 | 1 |
| Skew of Inertia for All - Fibrosis Texture | 7.41 | 5.62 | 1.93 | -1 |
| Kurtosis of Inertia for All - Fibrosis Texture | 64.93 | 37.12 | 3.17 | -1 |
| Normalized Count of Smooth of Entropy for All - Fibrosis Texture | 334.78 | 317.52 | 335.36 | 0 |
| Normalized Count of Rough of Entropy for All - Fibrosis Texture | 13.42 | 80.03 | 150.17 | 0 |
| Mean of Entropy for All - Fibrosis Texture | 0.68 | 2.03 | 3.24 | 0 |
| Median of Entropy for All - Fibrosis Texture | 0.42 | 1.75 | 2.33 | 1 |
| Std of Entropy for All - Fibrosis Texture | 0.87 | 1.13 | 2.13 | 1 |
| Skew of Entropy for All - Fibrosis Texture | 3.62 | 2.16 | 0.77 | 0 |
| Kurtosis of Entropy for All - Fibrosis Texture | 17.54 | 5.95 | -0.85 | 0 |

FIG. 9

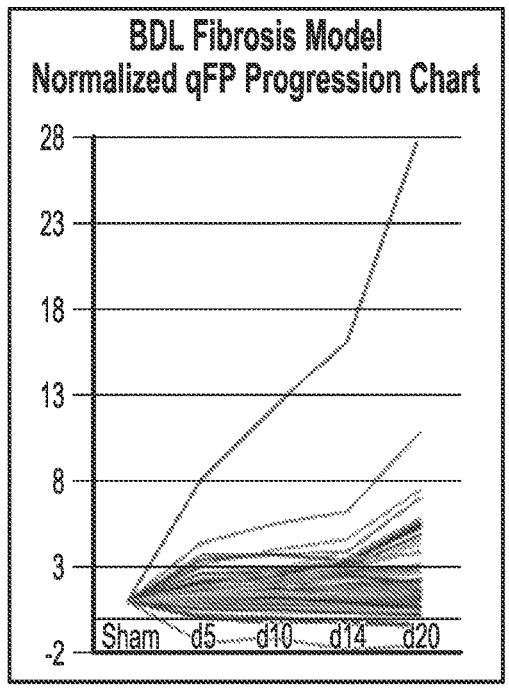
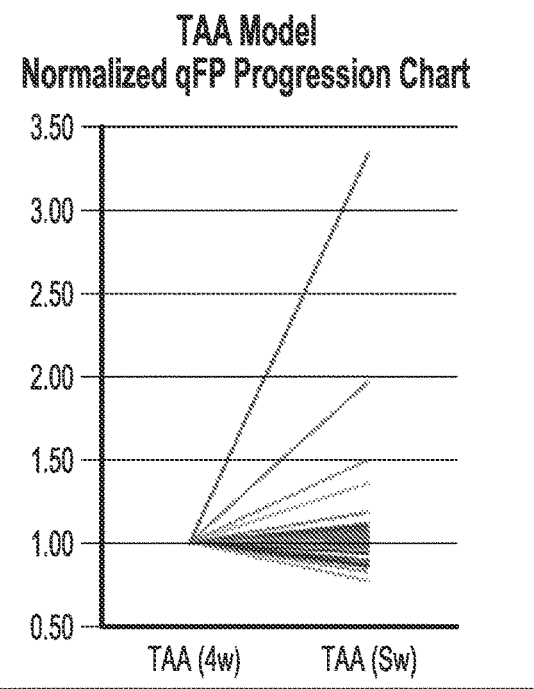
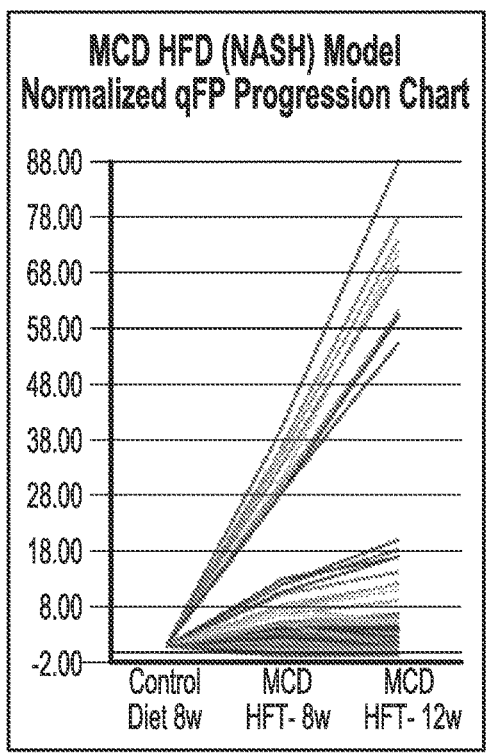
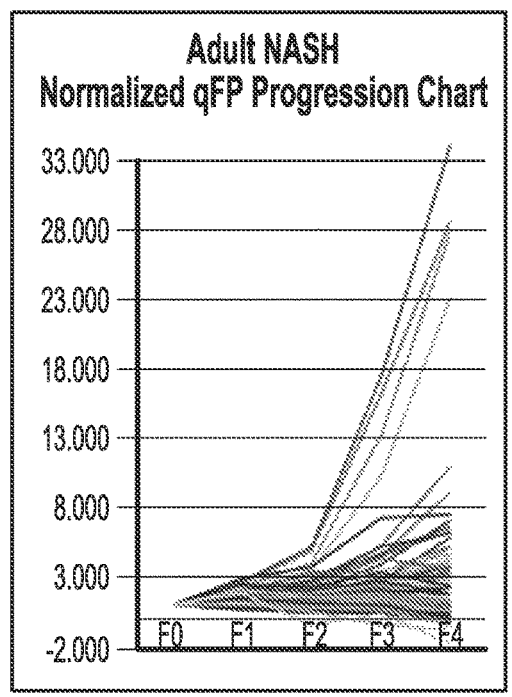
FIG. 11

FIG. 19

SYSTEMS AND METHODS FOR QUANTITATIVE PHENOTYPING OF FIBROSIS

CROSS-REFERENCE TO RELATED APPLICATIONS

This application is a continuation of U.S. patent application Ser. No. 16/851,881, filed Apr. 17, 2020, now U.S. Pat. No. 11,430,112, which claims the benefit of priority to U.S. provisional application Ser. No. 62/852,745, filed May 24, 2019 (now expired), which is hereby incorporated by reference in its entirety. This application is related to PCT Application Serial Number PCT/US2020/028813, filed Apr. 17, 2020, which is hereby incorporated by reference in its entirety.

TECHNICAL FIELD

This disclosure relates generally to quantitative assessment of fibrosis including, without limitation, computerized systems and methods that analyze a digital image taken of a biological tissue sample to quantitatively evaluate selected parameters that correlate with the phenotype of fibrosis, to quantify traits of the fibrosis phenotype in the biological tissue sample.

BACKGROUND

Fibrosis refers to the accumulation of collagen-based fibrous tissue in an organ when the organ attempts to repair and replace damaged cells but creates non-functioning scar tissue in place of functional tissue. There are different stages of fibrosis, and in its most severe form, the scar tissue destroys the organ's internal structure and, in the case of the liver, impairs its ability to regenerate. In the liver, this is referred to as cirrhosis and can cause portal hypertension, which can result in painful swelling and bleeding.

There are a variety of fibrotic conditions in multiple organs, such as liver, lung, kidney, heart, skin, uterus, muscle, adipose tissues, tissue from the gastric intestinal tract, and cancerous tissues in both human and animals. Some in-vitro models and meso-biological systems such as spheroids or printed organs can also develop fibrotic conditions. To some extent, the collagen-rich fibrous tissue (fibrosis) is necessary to structure organs and tissues because of its scaffold structure.

For liver, Non-Alcoholic SteatoHepatitis (NASH) is a severe form of non-alcoholic fatty liver disease (NAFLD) that can result in fibrosis and cirrhosis. While NASH is closely related to obesity, pre-diabetes, and diabetes, its symptoms are often non-specific to NASH, which makes it difficult to diagnose. Often, NASH patients are unaware of their condition until late stages of the disease. There are currently no medical treatments for NASH yet, but drug discovery efforts against NASH are ongoing.

For the lung, Idiopathic Pulmonary Fibrosis (IPF) is a type of chronic scarring of the lungs characterized by an irreversible progression of fibrosis resulting in a decline in lung function and death by suffocation. There are currently no satisfactory medical treatments for IPF yet, but drug discovery efforts against IPF are ongoing.

For skin, Scleroderma is a group of diseases that cause abnormal growth of the connective tissues due to excessive collagen (fibrosis) generation. Symptoms of scleroderma include calcium deposits in connective tissues, narrowing of blood vessels in the hands or feet, swelling of the esophagus, thick, tight skin on the fingers, and red spots on hands and face, all creating significant patient discomfort and handicaps. The causes of scleroderma are unknown, and there is no cure for scleroderma. However, various treatments can control and/or slow symptoms and complications. Drug discovery efforts against Scleroderma are ongoing.

To assess the extent of organ damage due to fibrosis, physicians can perform non-invasive testing such as blood tests and imaging tests, but the gold standard is to perform a biopsy by removing a tissue sample from the organ and using histopathology methods to evaluate the sample. This includes (1) fixing the tissue from the biopsy; (2) embedding the tissue in paraffin blocks; (3) sectioning the paraffin blocks to obtain thin sections of the tissue (typically 5 microns); (4) staining the sections with pathology stains; (5) imaging the stained tissues/sections by white light microscopy or digital white light microscopy; (6) quantifying specific tissue features, either by a pathologist, an automated image analysis, or both.

Pathologists use categorical scoring systems to assess the tissue biopsy and determine the extent of fibrosis. The METAVIR scoring system is commonly used to assess the liver biopsy to determine the extent of fibrosis in patients with hepatitis C. The NAKANUMA system is used to quantify the severity of fibrosis in Primary biliary cholangitis, another liver disease with no treatment. The ASHCROFT scale is used for determining the degree of fibrosis in lung specimens.

The NASH-CRN Fibrosis system classifies liver fibrosis in NASH patients into five stages, ranging from F0 to F4 (as indicated in the table below) and representing different amounts of fibrosis or scarring.

| | |
|---|---|
| F0 | No fibrosis, no scarring |
| F1 | Minimal scarring, or portal fibrosis without septa |
| F2 | Significant fibrosis, scarring has occurred and extends outside the liver area, portal fibrosis with few septa |
| F3 | Sever fibrosis, fibrosis spreading and forming bridges with other fibrotic liver areas, numerous septa without cirrhosis |
| F4 | Advanced scarring, cirrhosis |

However, the NASH-CRN Fibrosis scoring system is coarse in that it only defines five categories that range from no fibrosis (F0) to cirrhosis (F4). The scoring system is unable to distinguish between patients that are in one stage (e.g., F3), but are on opposite ends of that stage (e.g., closer to F2 or F4). For patients that are on opposite ends of the same stage, the plan for treatment may be different.

Similarly, all the current histological categorical scales used for the quantification of fibrosis are coarse and do not distinguish between patients on opposite ends of the same category. The same applies to histological systems used for the assessment of fibrosis in all kinds of biological tissues.

Moreover, current histological systems for the assessment of fibrosis in fibrosis-related conditions lack of accuracy and reproducibility. They are prone of a very high (up to 35%) intra- and inter-operator variability because these systems mostly relay on the elevation and scoring of histological by pathologists, which have variable level of experience, training or belong to different schools of thoughts.

Current methods apply the same general fibrosis stages that are used in humans (e.g., F0 through F4) for pre-clinical studies on animals. This assumes the scales developed on human studies are applicable to model the different stages and progression of fibrosis on animal models. This is problematic because, for example, some animal models for fibrosis do not exhibit septa, is used in part to define the F3 stage.

Current histological systems for the quantification of fibrosis are based on a very limited set of observable parameters, and are very poorly quantified by the human eye or simplistic quantification systems and exhibit very poor detection thresholds. They cannot quantify complex fibrosis phenotypes and, as a result, their utility is significantly limited to the staging of disease severity. This poses problems in the discovery and development of new drugs, or in the assessment and classification of patients to guide the management of their conditions.

Accordingly, current methods of measuring fibrosis are too simplistic and coarse (e.g., only four to six stages) to be able to distinguish even moderate changes in fibrosis, are subject to high intra- and inter-operator variability, and make assumptions regarding the similarity between human and animal models. Their performance limits the development of new drugs and biomarkers for fibrosis diseases, and the lack of phenotypic relevance limits the management of multiple forms of the fibrotic conditions across multiple species.

SUMMARY OF THE INVENTION

It is a goal of the present disclosure to improve upon the coarse methods of measuring fibrosis by implementing a phenotypic and continuous scoring system that provides increased dynamic range, and improved detection thresholds and incremental resolution to quantify the fibrosis phenotypes and their differences. The present disclosure provides systems and methods for tracking fibrotic disease progression on small time-scales, can be used to track the regression of fibrosis in response to a therapeutic compound or change in diet, and are suitable for describing the effect of investigational compounds in pre-clinical or clinical studies. In contrast to coarse stages of fibrosis, the present disclosure's phenotypic continuous scoring system distinguishes between the fibrosis phenotypes between two genetically different pools of animals or patients, and can distinguish between fibrosis conditions that have different aetiologies (for instance, liver fibrosis can be seen as a complication of obesity, diabetes, alcoholic steatosis, non-alcoholic steatosis, Hepatitis (B or C), etc.).

Because fibrosis is expressed as multiple forms and features across multiple organs and biological tissues, it is appropriate to describe and quantify fibrosis in a phenotypic way, using its composite observable characteristics or traits.

Accordingly, the present disclosure provides a way to measure fibrosis that has a wide dynamic range and fine resolution, because it has a continuous scale and a very high signal to noise ratio. Because the present disclosure incorporates a large number of selected quantifiable parameters to establish a composite score, the composite score provides a very high signal-to-noise ratio, resulting in high detection thresholds, improved sensitivity, and large dynamic ranges. As a result, the present disclosure is less prone to errors due to sources of noise from tissue processing or image acquisition. The quantitative nature of the present disclosure also ensures the system for measuring fibrosis is automated and not prone to large intra- and inter-operator variability. Moreover, the present disclosure is optimized for specific populations, such as pediatric versus adult patient populations, or specific animal models, and can even further be optimized for a specific organ in humans or a specific type of animal or biological tissue.

Accordingly, the phenotypic fibrosis scoring systems and methods presented herein can be used to do any of the following: quantify the severity and progression of fibrosis in a patient (or in another biological system), assess the response (or lack of thereof) of a patient (or any other biological system) to a therapeutic compound on short time-scales, and quantify the phenotype of fibrosis and its differences across species and genetic phenotypes, diseases conditions, stages, groups and sub-groups and aetiologies, treatments and response.

It is further an object of the present disclosure to quantify the phenotype of fibrosis in a biological tissue sample that considers multiple, if not all, the degrees of complexity of the collagens and its traits. As used herein, "fibrosis" includes all kinds of collagen-based structures, regardless of the chemical nature of the collagen. As used herein, "collagen" includes different types of collagens creating fibrosis, including collagen I, collagen III, etc. As used herein, "collagen object" corresponds to a representation of collagen, as depicted in a digital image. Identification of the collagen object in a digital image may result from pre-processing the digital image to indicate adjacent pixels or regions of the digital image that correspond to collagen. The collagen object may reflect adjacent pixels or regions of the digital image that correspond to the same type of collagen, and may be extracted from the digital image. As used herein, "collagens" corresponds to one or more collagen objects represented in a digital image, and may include the same or different types of collagen.

Described herein are systems and methods for quantifying a fibrosis phenotype. One aspect relates to computer aided phenotyping of fibrosis-related conditions. A digital image of a biological tissue sample is received, wherein the digital image indicates presence of collagens in the biological tissue sample. The image is processed to quantify a plurality of parameters, each parameter describing a feature of the collagens in the biological tissue sample that is expected to be different for different phenotypes of fibrosis. At least some of the features are selected from at least two of the group consisting of: (1) tissue level features that describe macroscopic characteristics of the collagens depicted in the digital image of the biological tissue sample; (2) morphometric level features that describe morphometric characteristics of the collagens depicted in the digital image of the biological tissue sample; and (3) texture level features that describe an organization of the collagens depicted in the digital image of the biological tissue sample. At least some of the plurality of parameters are statistics associated with histograms corresponding to distributions of the associated parameters across at least some of the digital image. At least some of the plurality of parameters in (b) are combined to obtain one or more composite scores that quantify a phenotype of fibrosis for the biological tissue sample.

In some implementations, at least one of the features is a tissue level feature, at least another feature in the features is a morphometric level feature, and at least another feature in the features is a texture level feature. At least two of the features may be tissue level features, at least another two features in the features may be morphometric level features, and at least another two features in the features may be texture level feature.

In some implementations, the at least some of the plurality of parameters that are combined corresponds to all of the plurality of parameters.

In some implementations, a first composite score of the one or more composite scores is specific to a feature type selected from the group consisting of tissue level, morphometric level, and texture level. A second composite score of the one or more composite scores may be specific to another feature type selected from the group consisting of tissue level, morphometric level, and texture level. The first and second composite scores may be combined to quantify the phenotype of fibrosis for the biological tissue sample.

In some implementations, the systems and methods are compatible with any modality of imaging that distinguishes between a presence and absence of collagens in the biological tissue sample. The systems and methods may be compatible with at least stained histopathology slides, two photon microscopy, fluorescence imaging, structured imaging, polarized imaging, Coherent anti-Stokes Raman Scattering (CARS), Optical Coherence Tomography (OCT) images, fresh tissue imaging, and endoscopy.

In some implementations, the depiction of collagens in the biological tissue sample results from an optical marker that is specific to any form of collagen. The optical marker may be selected from at least one of the group consisting of: (1) a collagen-specific stain used in a histopathology method; and (2) an intrinsic bio-optical marker specific to one or more collagens that is intrinsic to a modality of the digital image.

In some implementations, pixels of the digital image indicate presence and quantity of collagens in corresponding volumes of the biological tissue sample.

In some implementations, each of the texture level features characterizes different regions of the digital image by describing the collagen of each region. The different regions may correspond to non-overlapping or overlapping sample windows of the digital image. Quantifying a parameter describing a texture level feature may comprise: obtaining a sample value for each sample window, to obtain a plurality of sample values; generating a histogram of the plurality of sample values; and computing a statistic of the histogram as the parameter describing the texture level feature. The sample windows have the same or different sizes for different texture level features.

In some implementations, at least some of the parameters describing a morphometric level feature or a texture level feature is one of the statistics associated with histograms. In some cases, no parameters describing tissue level features are statistics associated with histograms. Sample values of the histograms for morphometric level features may correspond to individual fibers or bundles of fibers. Sample values of the histograms for texture level features may correspond to sample windows that identify subsets of the image. At least some of the plurality of parameters may result from processing the histograms.

In some implementations, the statistics associated with histograms are selected from the group consisting of (1) trend statistics including mean, median, mode, and normalized count, (2) distortion statistics including skew, (3) variance statistics including standard deviation, variance, outliers, and kurtosis, and (4) transition statistics related to cut-off values. The cut-off values may split the associated histogram into subsets of sample values, and each transition statistic is for a single subset of sample values. At least one of the histograms may be split by multiple cut-off values. The cut-off values may be determined by a user. The cut-off values may be different for different tissues. At least some statistics associated with histograms may be selected from the group consisting of trend statistics, distortion statistics, and variance statistics of individual subsets of sample values. Statistics associated with histograms may include normalized counts of individual subsets of sample values, wherein the normalized counts represent the number of sample values within the respective individual subset, normalized by the unit surface area of the digital image.

In some implementations, quantifying at least some of the plurality of parameters associated with histograms comprises processing the histograms to identify multiple modes of the histograms. Processing a histogram to identify multiple modes may comprise deconvoluting the histogram. Some modes of the histograms may correspond to phenotypic signatures of the fibrosis-related conditions, wherein deconvoluting the histogram comprises filtering the histogram to determine whether the histogram exhibits a phenotypic signature and to quantify the exhibited phenotypic signature.

In some implementations, the parameters that describe tissue level features include at least one selected from the group consisting of: collagen area ratio, large collagen object normalized density, small collagen object normalized density, and collagen network reticulation index.

In some implementations, the parameters that describe morphometric level features include at least one selected from the group consisting of: length, skeleton length, eccentricity, solidity, curvature ration, area, perimeter, and collagen density.

In some implementations, the parameters that describe texture level features include at least one relating to a collagen image pixel intensity level co-occurrence matrix, including at least one of the group consisting of: energy, homogeneity, correlation, inertia, entropy, skewness, and kurtosis.

In some implementations, the digital image is processed to distinguish between collagens in the biological tissue sample represented in the digital image. In this case, each of the plurality of parameters used to obtain at least one of the one or more composite scores may correspond to one class of collagen. The collagen classes may include one or more of fine collagen, assembled collagen, and tissue regions. Each of the plurality of parameters used to obtain the at least one of the one or more composite scores may correspond to the collagen class of fine collagen. Each of the plurality of parameters used to obtain the at least one of the one or more composite scores may correspond to the collagen class of assembled collagen. The plurality of parameters used to obtain the at least one of the one or more composite scores may correspond to both collagen classes of fine collagen and assembled collagen. The collagen classes may include one or more of long collagens and short collagens. The collagen classes may include one or more of high textured regions and low textured regions. The collagen classes may represent different levels of complexity in collagen skeleton.

In some implementations, at least some of the parameters describing morphometric features relate to one collagen class. In some implementations, at least some of the parameters describing tissue level features relate to one collagen class. In some implementations, the collagen classes distinguish different stages of fibrosis.

In some implementations, different features are selected to quantify different phenotypes of fibrosis. For example, parameters describing features of fine collagen fibers may be used to distinguish Fibrosis 0, Fibrosis 1, and Fibrosis 2. Parameters describing features of assembled collagen fibers may be used to distinguish Fibrosis 2, Fibrosis 3, and Fibrosis 4.

In some implementations, the plurality of parameters that are combined are selected from a list of candidate parameters. The plurality of parameters that are combined may be selected from the list of candidate parameters by identifying parameters that distinguish between different phenotypes of fibrosis. The identified parameters that distinguish between different phenotypes of fibrosis may be selected based on a calibration technique. The calibration technique involves a calibration data set of calibration digital images taken from biological samples having known phenotypes of fibrosis. In an example, the calibration technique involves principal component analysis to identify the selected parameters.

In some implementations, the selected parameters have less variance across the calibration data set for a given phenotype of fibrosis than unselected parameters. The known phenotypes of fibrosis may correspond to different outcomes of fibrosis disease. The known phenotypes of fibrosis may correspond to disease severity. The known phenotypes of fibrosis may correspond to NASH-CRN F disease stage, which include F0, F1, F2, F3, and F4. The known phenotypes of fibrosis correspond to different values or ranges of a fibrosis-related biomarker. The fibrosis-related biomarker may be indicative of progression of fibrosis and/or may be indicative of regression of fibrosis in response to treatment. The known phenotypes of fibrosis may correspond to different classes of fibrosis. The different classes of fibrosis may include NASH 1 and NASH 2.

In some implementations, the calibration technique selects parameters that have higher signal-to-noise than parameters that are not selected. Compared to the unselected parameters, the selected parameters may exhibit higher absolute differences for different phenotypes of fibrosis for the calibration data set. Compared to the unselected parameters, the selected parameters may exhibit lower standard deviations for the same phenotype of fibrosis for the calibration data set.

In some implementations, the combining of parameters may comprise assigning a weight to each parameter, wherein the absolute weight is higher for selected parameters that have lower standard deviation for the same phenotype of fibrosis for the calibration data set than other selected parameters. The weight may be negative for parameters that are negatively correlated with progression of fibrosis.

In some implementations, the list of candidate parameters includes over 300 candidate parameters, and the selected plurality of parameters consists of fewer than 35 parameters, fewer than 25 parameters, fewer than 15 parameters, 5 to 7 parameters, 2 to 5 parameters.

In some implementations, the calibration digital images are taken from biological samples of humans, wherein the calibration technique is specific to humans. The biological samples of humans may be taken from the same type of organ, wherein the calibration technique is specific to the same type of organ.

In some implementations, the calibration digital images are taken from biological samples of the same type of animal, wherein the calibration technique is specific to the same type of animal. The biological samples of the same type of animal may be taken from the same type of organ, wherein the calibration technique is specific to the same type of organ. The organ may be selected from the group consisting of the liver, lung, kidney, heart, skin, uterus, eye, gut, muscle, adipose tissue, tissue from the gastric intestinal tract, cancerous tissues both in human and animals, or any other organ or portion of the body that is susceptible to fibrosis.

In some implementations, the fibrosis-related conditions are selected from the group consisting of Hepatitis A, B or C, Non Alcoholic Steatosis Hepatitis (NASH), Alcoholic Steatosis Hepatitis (ASH), Cirrhosis, Primary Biliary Cholangitis and Primary biliary Cirrhosis, Idiopathic Pulmonary Fibrosis, Kidney Chronic Disease, Renal Disease, Scleroderma and Scaring, Duchenne muscular dystrophy, Myocardial infarction and repair, Macular Degeneracies, Glaucoma Uterine, and any manifestation of fibrosis in cancer.

In some implementations, the biological tissue sample is taken from a subject. The biological tissue sample may be tissue sampled from an organ of the subject that is susceptible to fibrosis. The organ may be a liver, lung, kidney, heart, skin, uterus, muscle, adipose tissues, tissue from the gastric intestinal track, cancerous tissues both in human and animals, or any other organ or portion of the body that, is susceptible to fibrosis. The subject may be a human, an animal, or a meso-biological system. The meso-biological system includes one or more spheroids, one or more printed organs, or a phenotypically relevant biosystem that is susceptible to fibrosis.

In some implementations, the digital image is taken of a biological cellular sample in vitro.

In some implementations, the severity of fibrosis of the biological tissue sample is quantified on a continuous scale. In some implementations, the progression of fibrosis for the subject is quantified on a continuous scale. In some implementations, the regression of fibrosis for the subject in response to a therapy, is quantified on a continuous scale. In some implementations, the type of fibrosis for the subject is quantified on a continuous scale.

In some implementations, effectiveness of a therapy or a drug candidate is evaluated. The therapy or drug candidate may be determined to be effective in a subject from which the biological tissue sample was taken. The therapy or drug candidate may be determined to be effective when it is determined that the therapy or drug candidate prevents progression of fibrosis in the subject.

In some implementations, the effectiveness of a drug candidate or a combination of drug candidates in a plurality of drug candidates is evaluated. The derivation of the one or more composite scores may be repeated for each sample in a plurality of samples, wherein at least some of the samples are treated with one of the drug candidates in the plurality of drug candidates. A rank may be assigned to each drug candidate in the plurality of drug candidates based on the one or more composite scores for the plurality of samples. The drug candidate with the highest rank may be selected as an effective drug candidate.

According to one aspect of the present disclosure, a subject with a fibrosis-related condition is treated, by determining one or more composite scores indicative of a phenotype of fibrosis for a biological tissue sample taken from the subject, using any of the systems and methods described herein; classifying the patient according to the phenotype in to select a treatment plan involving a therapeutic drug; determining an effective type and amount of the therapeutic drug based on the one or more composite scores; and administering the determined amount of the therapeutic drug to the subject.

In some implementations, the aforementioned steps are repeated a number of times to track progression of the fibrosis-related condition during treatment. The amount of the therapeutic drug may be adjusted based on whether the patient responds to treatment, as determined by the one or more composite scores.

According to one aspect of the present disclosure, a therapeutic drug is identified for use in treatment of a fibrosis-related condition, by determining one or more composite scores indicative of a predicted phenotype of fibrosis for a biological tissue sample taken from the subject, using any of the systems and methods described herein; administering a candidate drug to the subject; repeating the determining step to determine a fibrosis progression score of the subject over a period of time; and determining if the candidate drug is an effective therapeutic drug from the fibrosis progression score.

In some implementations, the plurality of parameters are selected from one or more, 10 or more, 50 or more, 100 or more, 150 or more, 200 or more, 250 or more, or 300 or more of the quantifiable fibrosis parameters listed in Appendix A.

BRIEF DESCRIPTION OF THE DRAWINGS

Further features of the disclosure, its nature and various advantages, will be apparent upon consideration of the following detailed description, taken in conjunction with the accompanying drawings, in which like reference characters refer to like parts throughout, and in which:

FIG. 3 depicts a set of exemplary digital images with corresponding exemplary tissue level parameters, according to an illustrative implementation;

FIG. 4 depicts an exemplary data structure that stores mean values of example tissue level parameters, representing different features of collagen depicted in digital images of the calibration data set, taken from biological samples having known fibrosis stages in biopsies of adult patients with Liver NASH (F0, F2, F4), according to an illustrative implementation;

FIGS. 5-6 depict the same set of exemplary digital images as shown in FIG. 3, with corresponding exemplary morphometric level parameters for the length (FIG. 5) and the eccentricity (FIG. 6) of the collagen objects identified in the digital image, their histogram distribution and some of the related histogram analysis quantitative parameters, according to an illustrative implementation;

FIG. 7 depicts an exemplary data structure that stores the results of the histogram analysis of some examples of morphometric level parameters, representing different features of collagen depicted in digital images of the calibration data set, taken from liver biopsies of adult patients with NASH having known fibrosis stages (F0, F2, F4), according to an illustrative implementation;

FIG. 9 depicts an exemplary data structure that stores mean values of example texture level parameters, representing different texture organizational features of collagen depicted in digital images of the calibration data set, taken from liver biopsies of adult patients with NASH having known fibrosis stages (F0, F2, F4), according to an illustrative implementation;

FIG. 11 depicts exemplary normalized values for quantitative parameters in a calibration data set for different fibrosis phenotypes for a specific population, according to an illustrative implementation;

DETAILED DESCRIPTION

Figure 1:
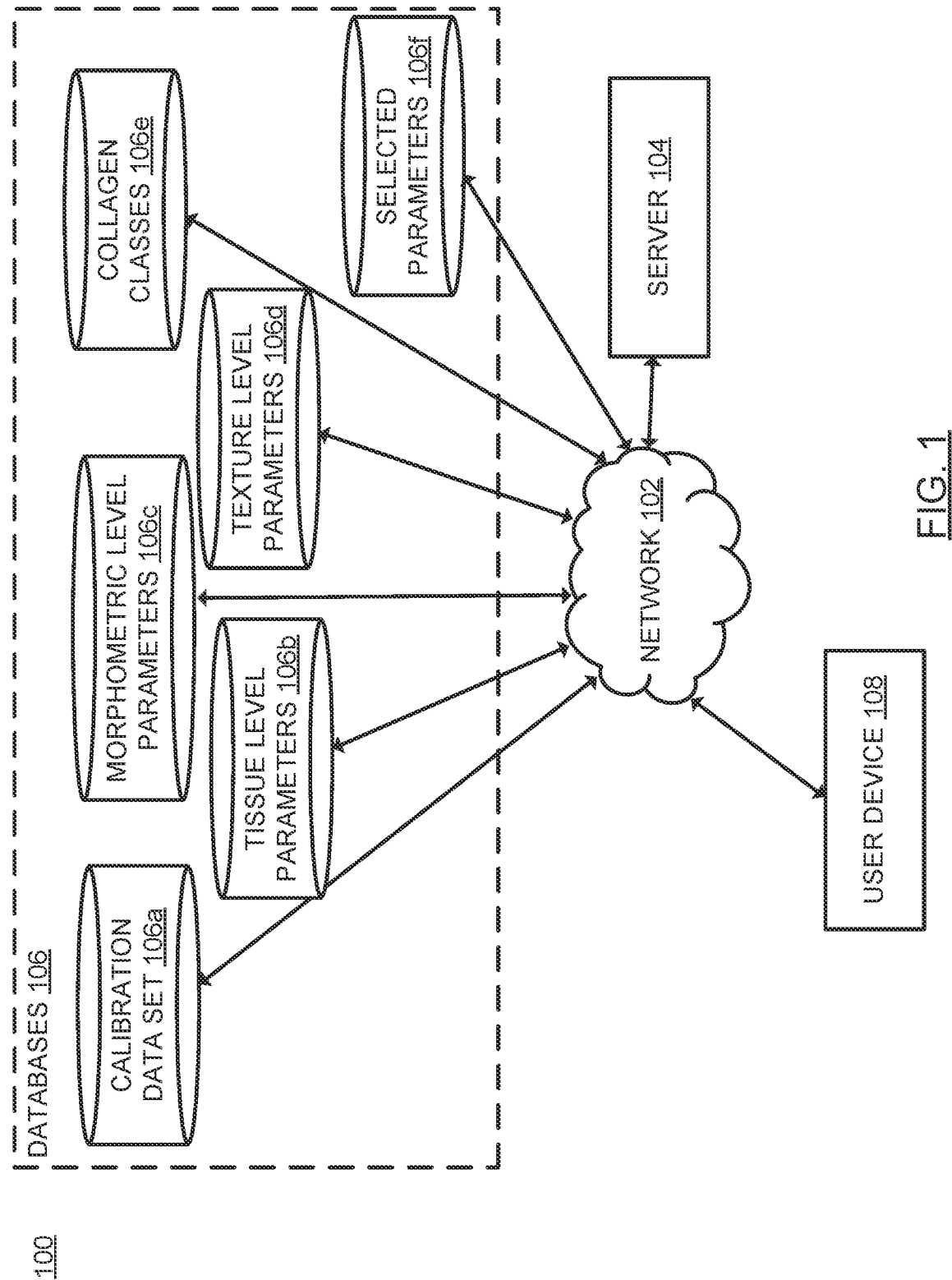
FIG. 1 depicts an exemplary system for quantifying a phenotype of fibrosis, according to an illustrative implementation.

To provide an overall understanding of the systems and methods described herein, certain illustrative embodiments will now be described, including systems and methods for quantifying the phenotype of fibrosis from digital images of biological tissues. However, it will be understood by one of ordinary skill in the art that the systems and methods described herein may be adapted and modified for other suitable applications, such as any data classification application, and that such other additions and modifications will not depart from the scope thereof. Generally, the computerized systems described herein may comprise one or more engines, which include a processor or devices, such as a computer, microprocessor, logic device or other device or processor that is configured with hardware, firmware, and software to carry out one or more of the computerized methods described herein.

The present disclosure relates to systems and methods for quantifying the phenotype of fibrosis (corresponding to the fibrosis observable traits) from a digital image of any tissue. The digital image reflects an optical biomarker that is specific to the collagens present in the tissue. The systems and methods for quantifying the fibrosis phenotype may be automated, and provide a continuous quantification of fibrosis in any kind of biological tissue from any digital image that depicts collagens in the biological tissue.

The digital image is generally an image of a biological tissue prepared and stained for collagen and digitally acquired by Whole Slide Imaging (WSI) methods. The present disclosure is not limited to any specific tissue imaging method, so long as the digital image includes a distinguishing marker specific to one or multiple collagen molecules versus non-collagen molecules. The biological tissue could be from a human, animal or from any other biological system, and may be taken from the liver, lung, heart, muscle, skin, kidney, gut, uterus, eye, adipose tissue, tissue from the gastric intestinal tract, cancerous tissues in humans or animals, or any other organ or portion of the body or phenotypically relevant biosystem that is susceptible to fibrosis. The digital image may include a two-dimensional digital image(s), a three-dimensional digital image(s), a digital image stack(s), a static digital image(s), a time-course series of digital images, a digital movie(s), or any suitable combination thereof. The digital image includes an optical marker specific to collagen, either from collagen-specific stains used in histopathology methods, or from intrinsic bio-optical markers specific to collagen (and fibrosis) intrinsic to the optical imaging method (such as second harmonic generation) fibrosis, or in more general terms to any kind of collagen.

As used herein, an organ includes any of the aforementioned bodies or body portions, or it may include meso-biological systems such as spheroids or printed organs that can also develop fibrotic conditions. Generally, an organ can include any phenotypically relevant biosystem that is susceptible to fibrosis.

It is an object of the present disclosure to provide automated and continuous quantification of the fibrosis phenotype in any kind of digital image indicating the presence of one or more collagens from of any kind of biological tissue. In contrast to a categorical approach that only coarsely defines the stages of fibrosis as one of a small number (e.g., 4-6) stages, an approach that uses continuous quantification uses a continuous scale to quantify the fibrosis. The continuous scale allows for precise tracking of fibrosis progression even on short timescales, and allows for tracking of response to treatment or treatment candidates of fibrosis. It also allows for the system to distinguish and classify tissues with different phenotypes of fibrosis (e.g., with possibly the same amount or basic features of collagen), and/or to develop biomarkers for fibrosis (as the continuous quantification of fibrosis can be used to establish robust correlation with the continuous values of the biomarker candidates). The present disclosure provides a scoring system for fibrosis that is continuous, and offers improved signal-to-noise ratio, detection threshold and dynamic range so that it can precisely quantify the fibrosis phenotype.

The present disclosure has clinical applications in quantifying fibrosis of human patients, but also has pre-clinical applications in animal and other biological models. The fibrosis phenotypes correspond to fibrosis-related conditions having different outcomes of fibrosis disease. In one example, the fibrosis phenotypes correspond to disease severity, and may correspond to NASH-CRN F disease stages, which include F0, F1, F2, F3, and F4. In one example, the fibrosis phenotypes correspond to different values or ranges of a fibrosis-related biomarker that is indicative of progression (or regression) of fibrosis, severity of fibrosis, response to treatment, or any combination thereof. In one example, the fibrosis phenotypes correspond to different classes of fibrosis, such as NASH 1 versus NASH 2 in pediatric populations with NASH. Any of these examples of fibrosis phenotypes may be present in human and animal biological tissues and accordingly have both clinical and pre-clinical applications. In some implementations, a digital image of a biological tissue sample is assessed for multiple fibrosis phenotypes at the same time. Specifically, different composite scores may be assessed on the same digital image, where each composite score represents a different fibrosis phenotype. For example, for a patient suffering from a fibrotic condition, a fibrosis severity composite score, a fibrosis progression composite score, and a fibrosis type composite score may be assessed in parallel from the same digital image of a biopsy to determine how severe the disease is, how fibrosis is progression in the subject, and to classify the type of fibrosis in the subject, respectively.

The figures of the present disclosure are described below in detail and illustrate exemplary systems, methods, data structures, and graphs that provide a robust and accurate way to quantitatively characterize fibrosis. The figures further demonstrate that the quantitative approaches described herein improve upon existing categorical approaches to quantify fibrosis severity by having a continuous scale that allows a composite score to closely track progression of fibrosis as it worsens, and regression of fibrosis in response to treatment or therapy.

Figure 2:
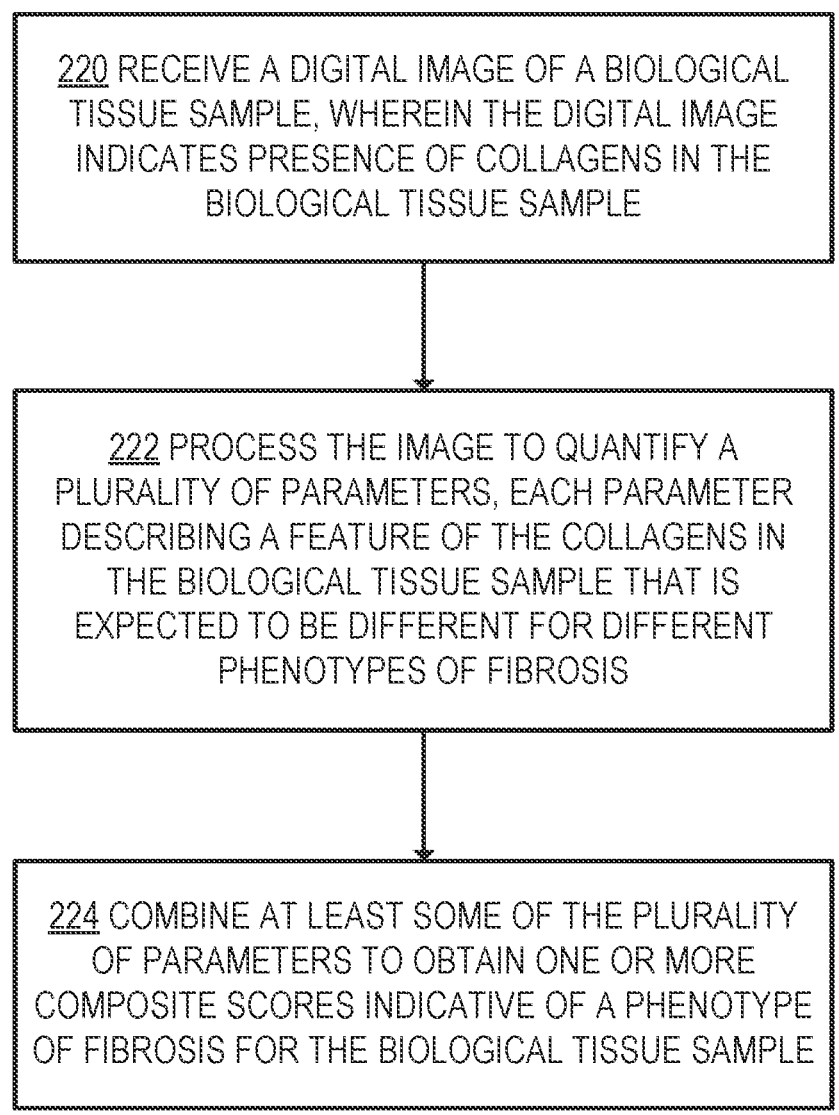
FIG. 2 is a high-level flow diagram of a process for quantifying a phenotype of fibrosis in a digital image of a biological tissue sample, according to an illustrative implementation.
Figure 6:
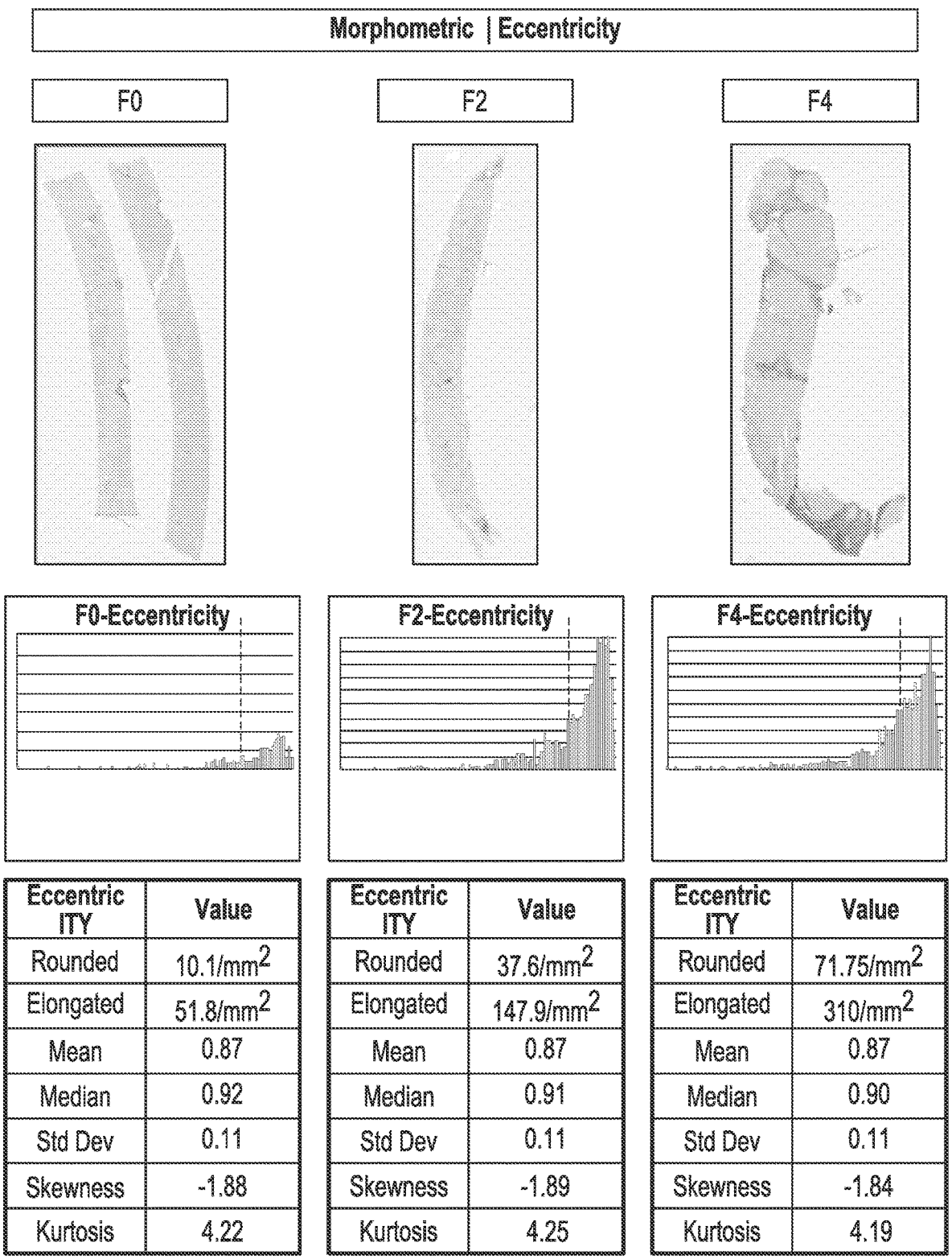
Figure 8:
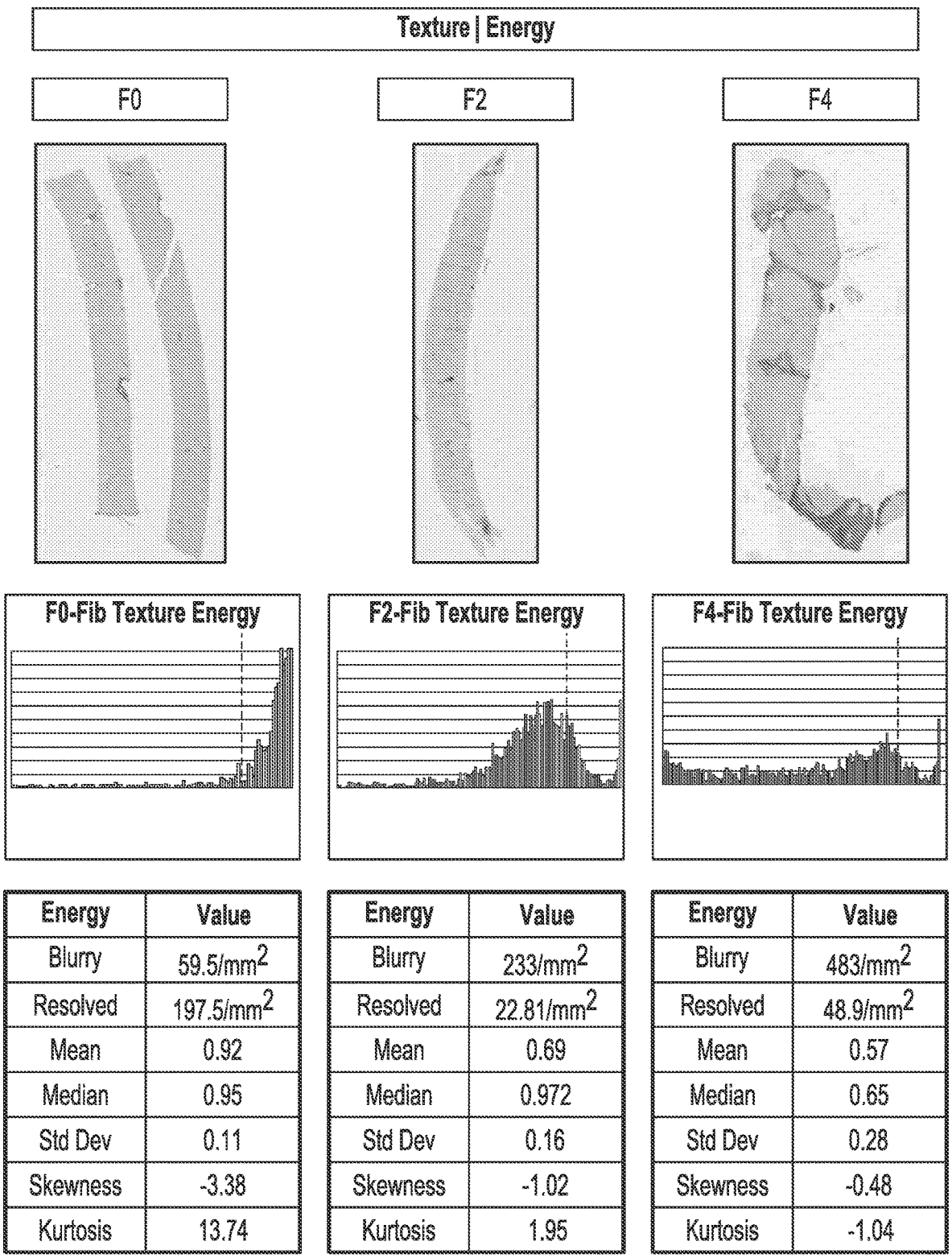
FIG. 8 depicts the same set of exemplary digital images as shown in FIGS. 3 and 5-6, with corresponding exemplary texture level parameters, their histogram distribution and some of the related histogram analysis quantitative parameters, according to an illustrative implementation.
Figure 10:
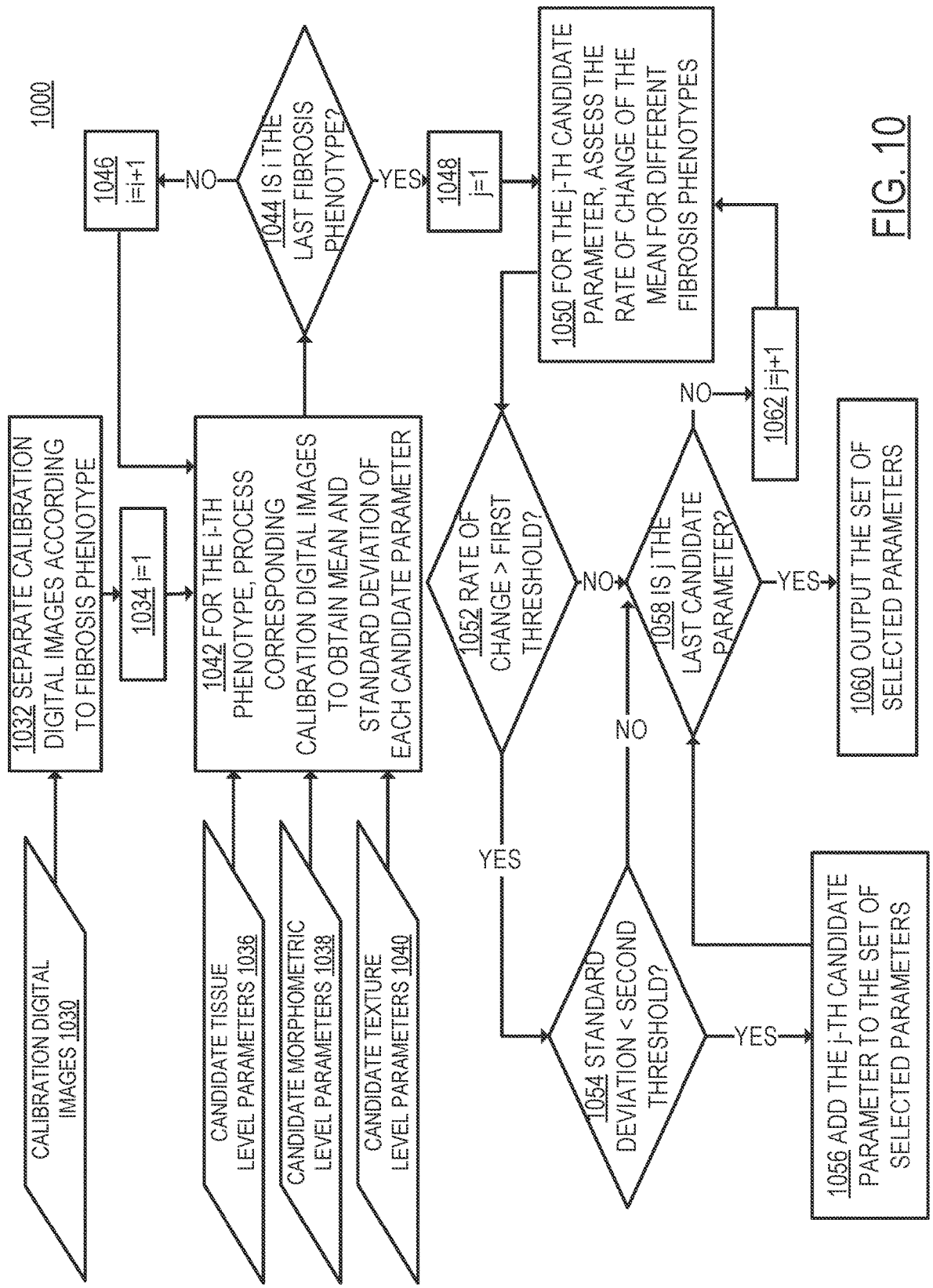
FIG. 10 is an exemplary flow diagram of a calibration process for selecting parameters to include in a calculation of a composite score for quantifying a phenotype for fibrosis for a specific population, according to an illustrative implementation.
Figure 12:
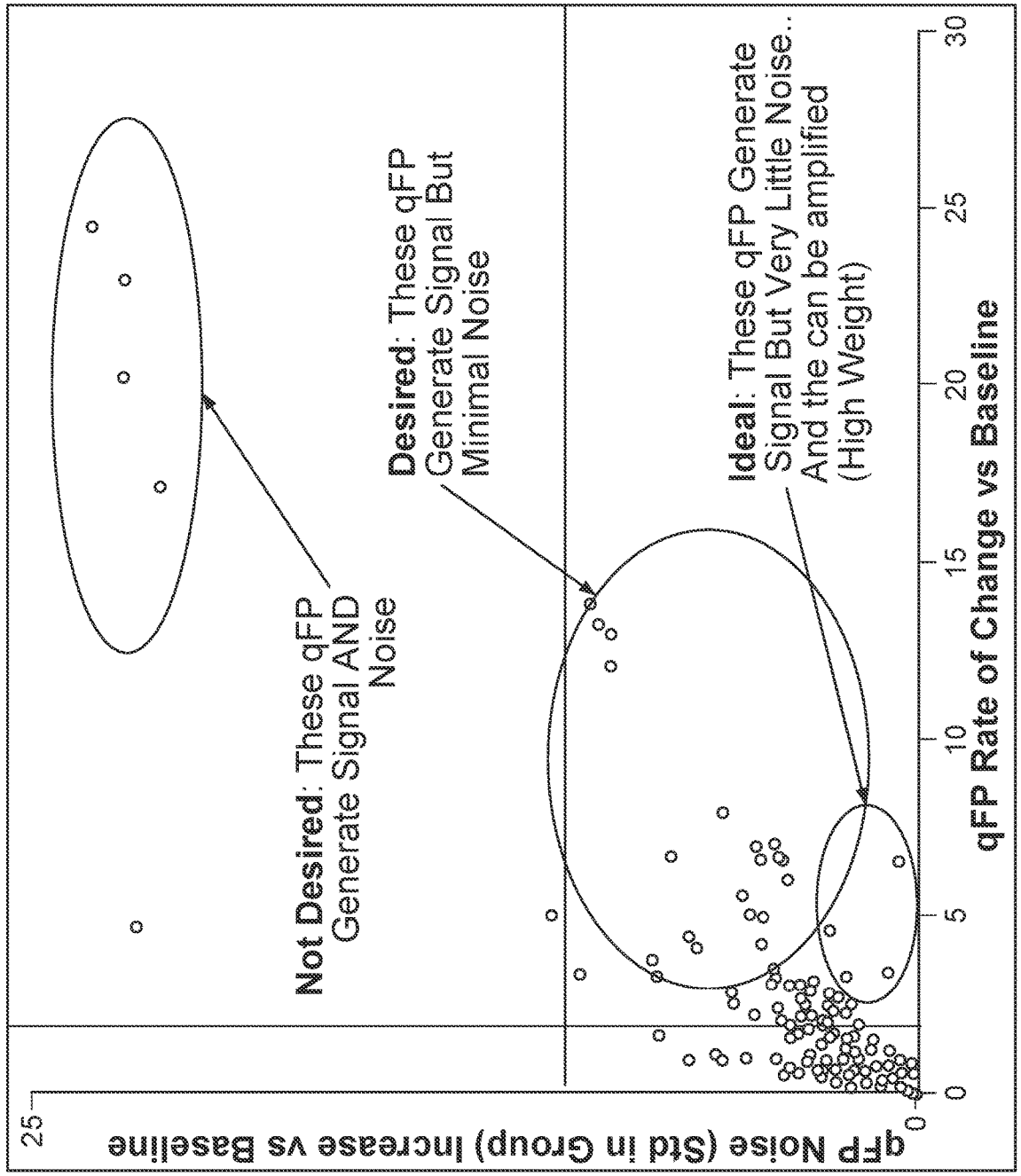
FIG. 12 depicts a plot showing the noise versus rate of change of various quantitative parameters in a calibration data set for a specific population, according to an illustrative implementation.
Figure 13:
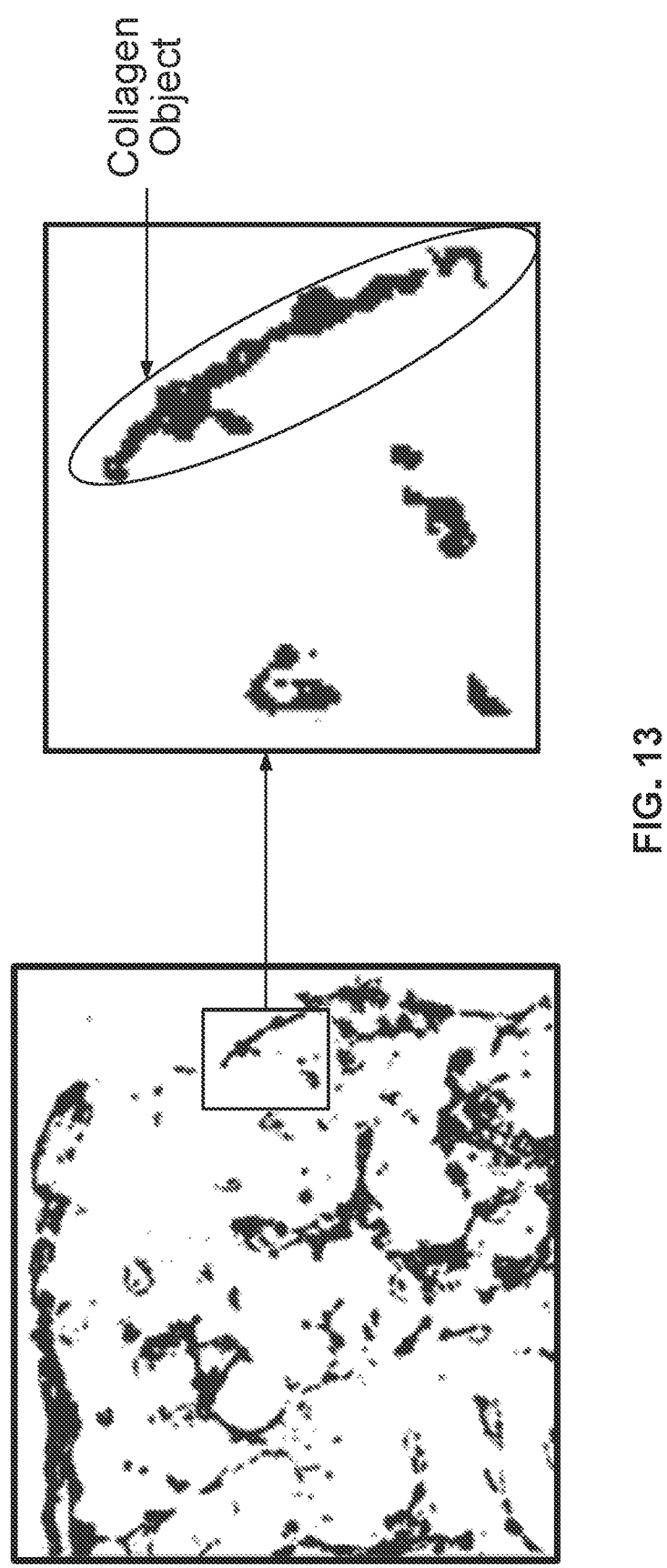
FIG. 13 depicts a processed version of an exemplary digital image, in which certain areas of the image are recognized as collagen (black pixels) and a collagen object is extracted from the image, according to an illustrative implementation.
Figure 14:
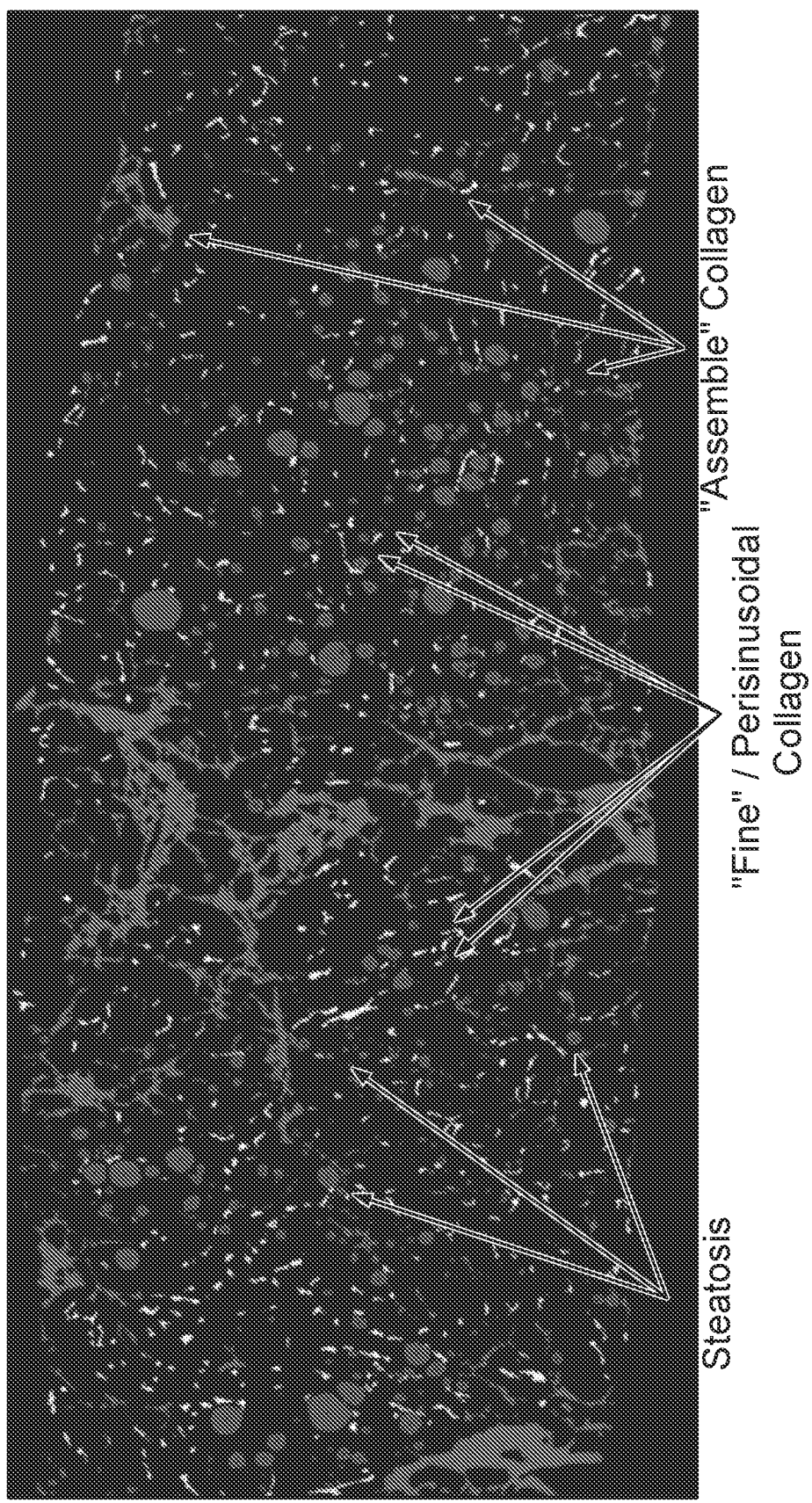
FIG. 14 depicts a processed version of an exemplary digital image, in which different collagen features, including steatosis, fine (or "perisinusoidal" in the case of liver) collagen, and assembled collagen are extracted, according to an illustrative implementation.
Figure 15:
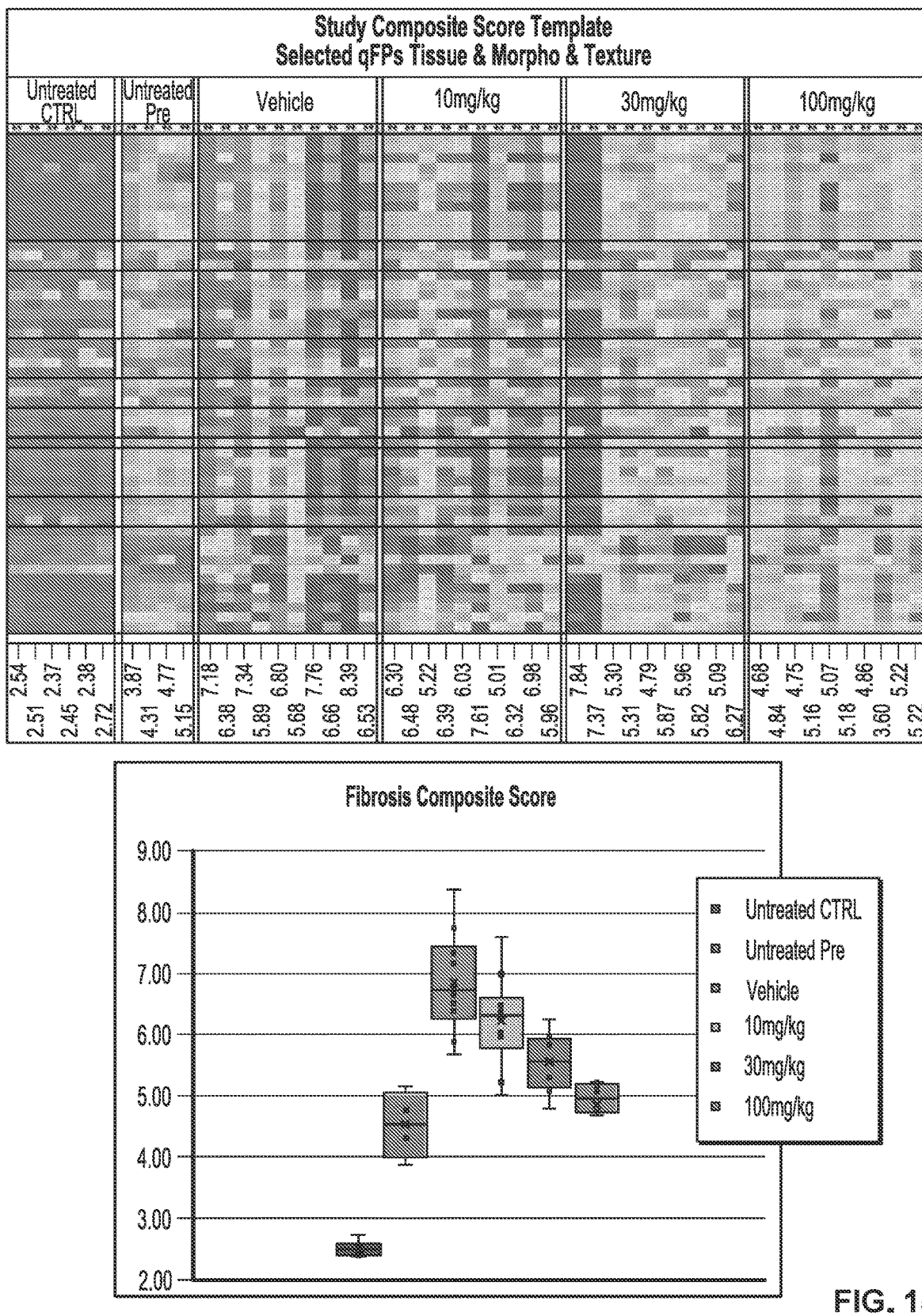
FIG. 15 depicts on the left, a heat map of a set of selected quantitative parameters (y-axis) describing collagen features in a calibration data set for different populations, including control, untreated, vehicle, and treated at different doses (10, 30, and 100 mg/kg), and on the right, a bar graph showing the fibrosis composite score is able to track the different stages of disease, including response to treatment, according to an illustrative implementation.
Figure 16:
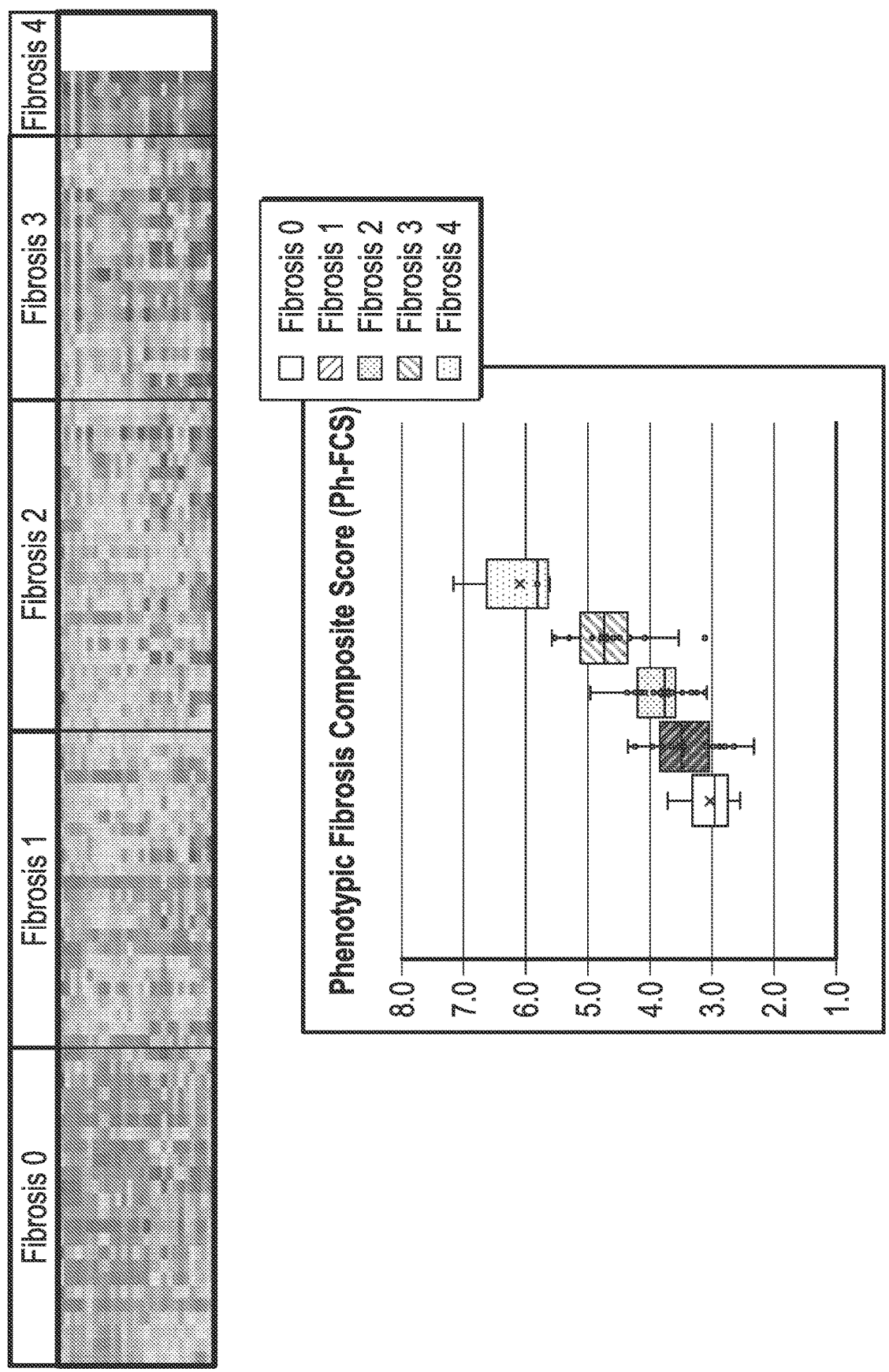
FIG. 16 depicts on top, a heat map of a set of selected quantitative parameters (y-axis) describing collagen features in a calibration data set for liver biopsies of adult patients with NASH, including F0, F1, F2, F3, and F4 (x-axis), and on the bottom, a bar graph showing the fibrosis composite score is able to track the different stages of the disease, according to an illustrative implementation.
Figure 17B:
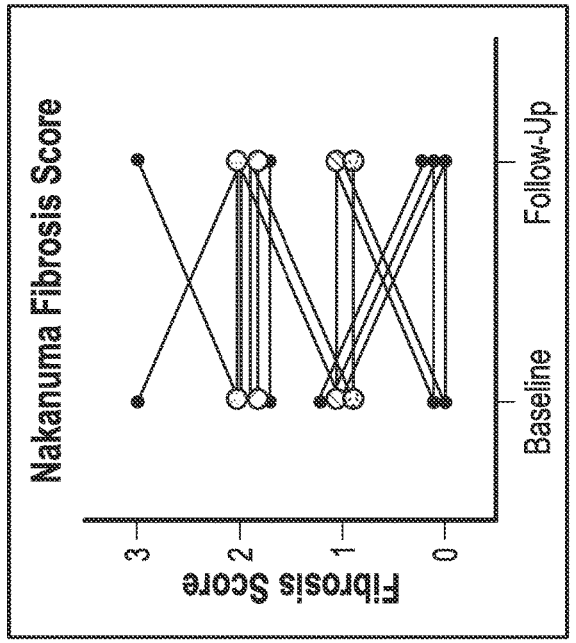
FIG. 17 depicts data indicating how the composite score, developed to quantify the severity of fibrosis in adult patients suffering from Primary Biliary Cholangitis, correlates with the Nakanuma fibrosis stages (FIG. 17A), and provides a continuous assessment of changes (in this case reduction) of fibrosis in a cohort of patients from baseline to follow up (after treatment) biopsies (FIG. 17C) and resolving the improvement changes within the buckets of the Nakanuma categorical scores (FIG. 17B), according to an illustrative implementation.
Figure 17A:
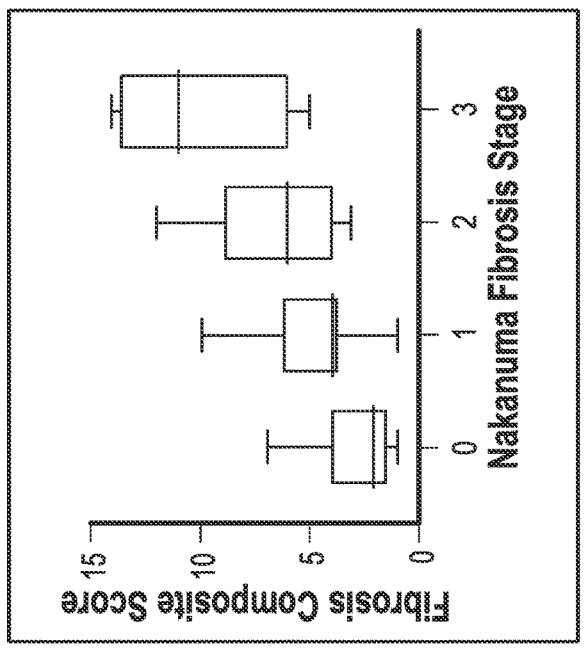
Figure 17C:
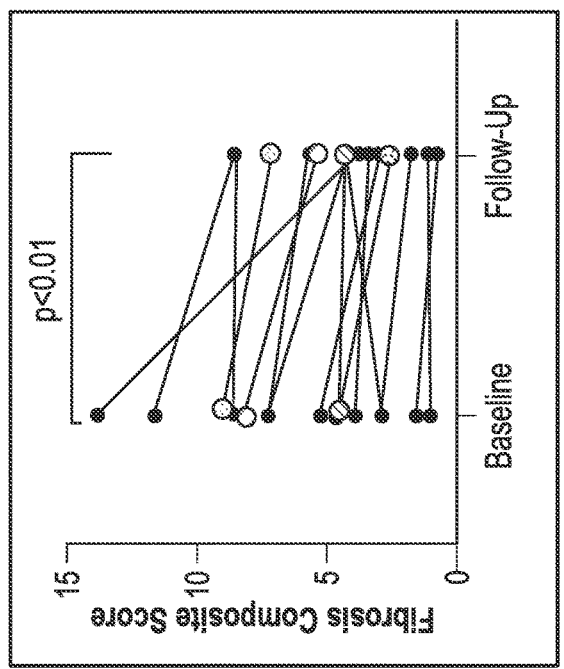
Figure 18:
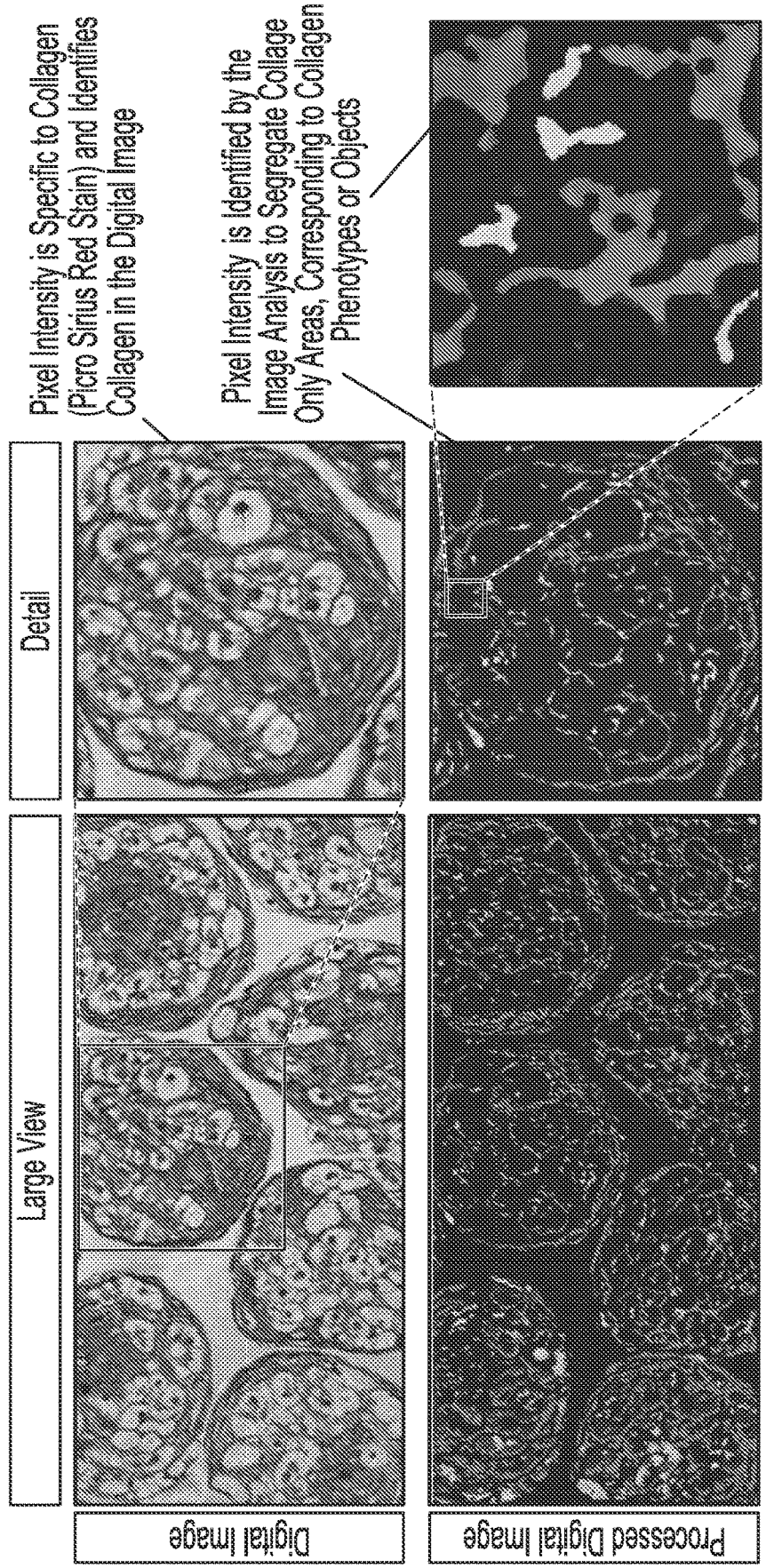
FIG. 18 depicts a processed version of an exemplary digital image, in which certain regions of the digital image are recognized as collagen (gray pixels), and the collagen is organized into various collagen objects of different collagen classes (indicated by different grayscale intensities, according to an illustrative implementation.
Figure 19:
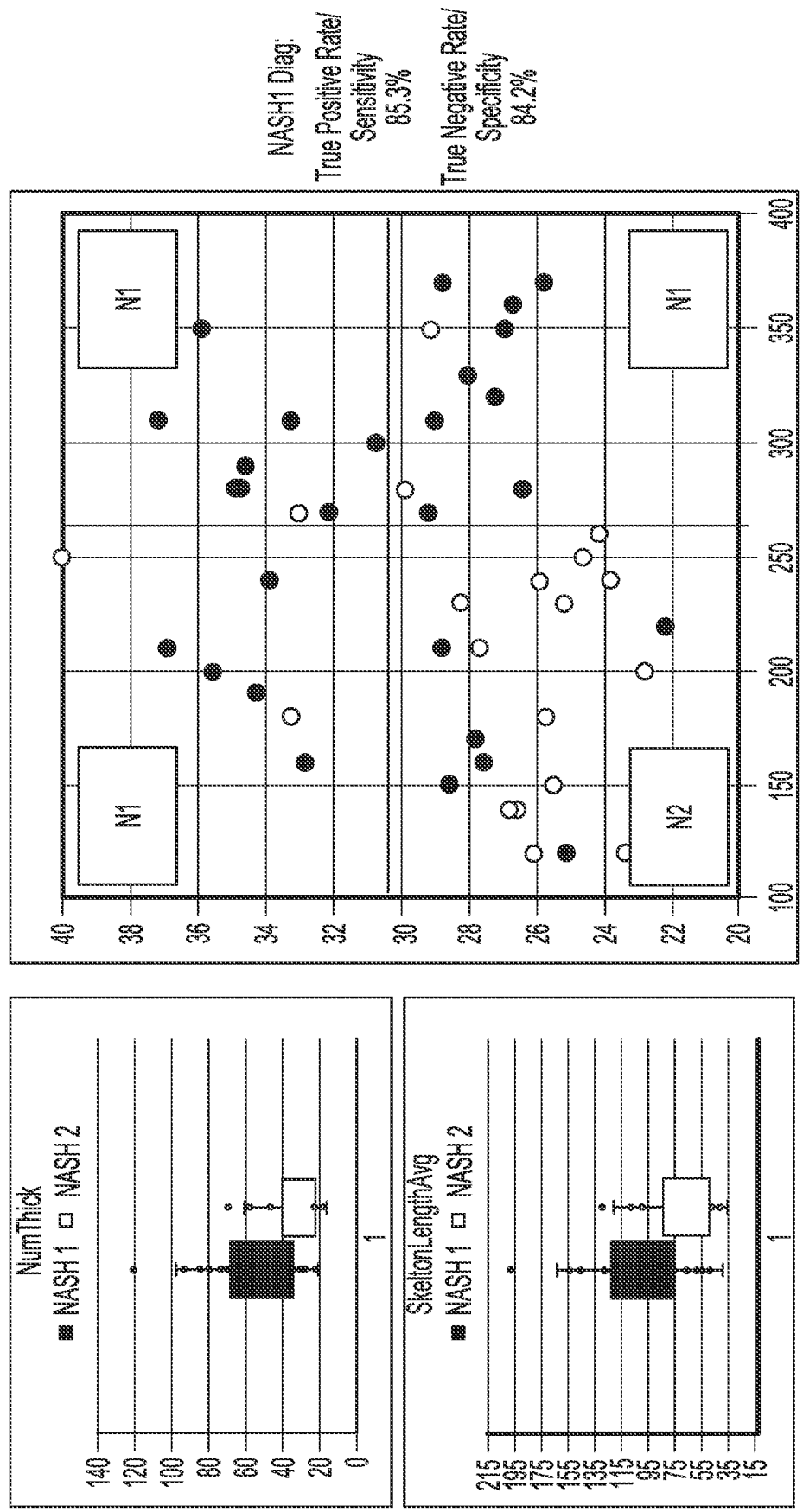
FIG. 19 depicts data indicating how the composite score, developed to distinguish between NASH 1 and NASH 2 patients, performs well when the score is based on two top-performing parameters selected from a set of candidate parameters, according to an illustrative implementation.

Specifically, FIGS. 1-2 depict a representative system 100 (FIG. 1) and a high level flow diagram 200 (FIG. 2) for implementing the systems and methods of the present disclosure, for quantifying the phenotype of fibrosis. FIGS. 3-9 show exemplary ways to extract various data from digital images taken of biological tissue samples having differing severity of fibrosis as defined by pathologists and widely proven by patient outcomes. Namely, the present disclosure relates to at least three levels of quantitatively characterizing fibrosis from an image. As used herein, different levels of quantitatively characterizing fibrosis from an image correspond to different ways of characterizing the appearance and organization of collagens in the image. Specifically, the different levels of the present disclosure relate to macroscopic characteristics of the collagens (tissue level), morphometric characteristics of the collagens (morphometric level), and organizational characteristics of the collagens (texture level). Each of these levels is described in further detail below. FIGS. 3-4 relate to tissue level features that describe macroscopic characteristics of the collagens depicted in the digital image. FIGS. 5-7 relate to morphometric level features that describe morphometric characteristics of the collagens depicted in the digital image, and their relative histogram distributions from which several quantitative parameters are extracted. FIGS. 8-9 relate to texture level features that describe collective and regional organizations and shapes of the collagens depicted in the digital image, and their relative histogram distributions from which several quantitative parameters are extracted. FIGS. 10-12 relate to an illustrative method and example histogram plots for selecting which of the various quantitative parameters representing the features described in relation to FIGS. 3-9 to include in the generation of a composite score for representing the phenotype of fibrosis on a continuous scale. FIGS. 13-14 and 18 depict exemplary digital images that are pre-processed to identify collagen objects in tissue samples. FIGS. 15-17 show that the phenotypic composite score of the present disclosure is able to track severity of fibrosis as well as regression of fibrosis, in response to treatment for instance, and improves upon known coarse categorical approaches to defining the fibrosis phenotype. FIG. 19 indicate that the phenotypic composite score of the present disclosure is able to classify patients as NASH 1 versus NASH 2.

FIG. 1 depicts an exemplary system 100 for quantifying the phenotype of fibrosis from a digital image containing collagen-specific information in tissue, according to an illustrative implementation. The system 100 includes a server 104 and a user device 108 connected over a network 102. The server 104 and the user device 108 each include one or more processors to perform any of the methods or functions described herein. As used herein, the term "processor" or "computing device" refers to one or more computers, microprocessors, logic devices, servers, or other devices configured with hardware, firmware, and software to carry out one or more of the computerized techniques described herein. Processors and processing devices may also include one or more memory devices for storing inputs, outputs, and data that is currently being processed.

The user device 108 may include, without limitation, any suitable combination of one or more devices configured with hardware, firmware, and software to carry out one or more of the computerized techniques described herein. Examples of user devices include, without limitation, personal computers, laptops, and mobile devices (such as smartphones, blackberries. PDAs, tablet computers, etc.). The user device 108 includes a user interface, that includes, without limitation, any suitable combination of one or more input devices (e.g., keypads, touch screens, trackballs, voice recognition systems, etc.) and/or one or more output devices (e.g., visual displays, speakers, tactile displays, printing devices, etc.). While only one server and one user device are shown in FIG. 1 to avoid complicating the drawing, the system 100 can support multiple servers and multiple user devices.

In some implementations, the user device 108 is a mobile device such as a smartphone or tablet. In general, one benefit of the systems and methods of the present disclosure is that they do not require particularly high resolution digital images. Even digital images with relatively low resolution, such as those captured on a device such as a smartphone or tablet, are able to be used with the techniques of the present disclosure, to quantify the fibrosis phenotype in a subject. For example, the user device 108 may be capable of receiving a small plug-in device having a receptacle or a slot that holds a glass slide, such as a microscope slide containing the biological tissue sample, in place. The plug-in device may be configured to ensure uniform lighting for the slide, so that a camera on the user device 108 adequately captures the collagens in the tissue sample in a reproducible manner.

The components of the system 100 are depicted as being connected over a network 102. The arrangement and numbers of components shown in FIG. 1 are merely illustrative and any suitable configuration may be used. For example, although FIG. 1 depicts system 100 as a network-based system for quantifying the phenotype of fibrosis, the functional components of the system 100 may be implemented as one or more components included with or local to the user device 108, that includes a processor, a user interface, and an electronic database. The processor of the user device 108 may be configured to perform any or all of the functions of the processors of the server 102. The electronic database of the user device 108 may be configured to store any or all of the data stored in database 106 of FIG. 1. Additionally, the functions performed by the components of the system 100 may be rearranged. For example, the server 104 may perform some or all of the functions of the user device 108, and vice versa.

The database 106 is a distributed system of databases that includes a "calibration data set" database 106a, candidate parameter databases including "tissue level parameters" database 106b, "morphometric level parameters" database 106c, "texture level parameters" database 106d, "collagen classes" database 106e, and "selected parameters" database 106f. As depicted in FIG. 1, each database is a separate database, but any of the databases shown in FIG. 1 may be combined into a common database. For example, the candidate parameter databases 106b-d may be combined together into a single database, which may further be combined with the collagen classes database 106e, the calibration data set database 106a, or both.

The calibration data set database 106a includes a set of calibration digital images taken from biological samples having known phenotypes of fibrosis, which may be stored in metadata corresponding to the digital images. Multiple sets of calibration digital images may be stored in the calibration data set database 106a, where the different sets of images correspond to different fibrosis phenotypes, such as severity of fibrosis, type of fibrosis, or different stages of progression or regression of fibrosis. The digital image is generally an image of a biological tissue prepared and stained for collagen and digitally acquired by Whole Slide Imaging (WSI) methods. The biological tissue could be from a human, animal or from any other biological system, and may be taken from the liver, lung, heart, muscle, skin, kidney, gut, uterus, eye, adipose tissue, tissue from the gastric intestinal tract, cancerous tissues in human or animals, or any other organ or portion of the body or phenotypically relevant biosystem that is susceptible to fibrosis.

Each calibration digital image is accompanied by metadata associated with the image, such as data regarding the patient or animal (e.g., species, age, gender, genotype, race, blood or genetic biomarker data.), the nature, characteristics, locations of the collagen biomarker (e.g. Second Harmonic Generation channel, or type and color of the histopathology collagen specific marker), image annotations on the image (e.g., regions of the image to exclude from the analysis), the fibrosis phenotype or severity stage of fibrosis as assessed by a physician, pathologist, or any other expert, body region or organ that is depicted in the image, whether the patient or animal has been treated for fibrosis or another medical condition and the corresponding treatment protocol, or any other suitable patient data), and/or data regarding the image (e.g., when the image was taken, the imaging modality, image dimensions, or any other suitable image data).

The set of calibration digital images stored in the calibration data set database 106a may include multiple subsets of calibration digital images, corresponding to different patient or animal populations, which may be further grouped according to specific sub-populations. The sub-populations may include control groups having no disease and one or more disease states, and test groups having variable treatment plans, such as different dosages of a drug or therapy. In an example, the sub-populations correspond to wild-type and genetically modified animal models such as knock-out animals, so that the present disclosure can be used to study the physiological mechanisms of fibrosis, its progression, and response to treatment, or to identify and quantify traits of fibrosis that are different from such two genetic models, or to establish a scoring technique that can be used to classify such two models in a blinded way.

The candidate parameter databases 106*b-d* include candidate parameters, each of which is a quantitative measurement that characterizes the calibration digital images in the calibration data set 106*a*. The candidate parameters and examples of how they are derived from individual digital images are described in detail below, with reference to FIGS. 3-9. Briefly, the candidate parameters quantitatively assess the digital images at three different levels. Specifically, for the collagens depicted in a digital image, tissue level parameters quantify macroscopic characteristics of the collagens, morphometric level parameters quantify morphometric (e.g., shape and size) characteristics of the collagens, and texture level parameters quantify an organization of the collagens. While parameters at any one level may sometimes be sufficient for characterizing the fibrosis phenotype in a subject, combining parameters from different levels (e.g., two or three levels) generally results in a robust and accurate method to quantify phenotype of fibrosis.

The collagen classes database 106*e* represent various classes of collagen that may be depicted in the calibration digital images. The collagen class corresponds to a specific type of collagen that is depicted in the image, which may exhibit differently for different fibrosis phenotypes. Thus, using quantitative parameters (e.g., any of the candidate parameters described in relation to 106*b-d*) that are specific to one or more particular collagen classes may further improve robustness and accuracy of the present disclosure. In fact, any of the candidate parameters in databases 106*b-d* may reflect total collagen depicted in an image, one specific collagen class depicted in the image, or multiple, but not all, collagen classes depicted in the image.

Example collagen classes include single collagen fibers, bundles of collagen fibers, diffuse collagen tissue regions, fine collagen, assembled collagen, tissue regions, long collagens, short collagens, high textured regions, low textured regions, highly complex collagen skeleton, less complex collagen skeleton, any other suitable type of collagen, or any combination thereof. FIGS. 13, 14, and 18 depict example representations of how the system identifies different collagen objects in an image, and how the system distinguishes between different collagen classes such as fine collagen and assembled collagen, respectively. Specifically, the system may perform image processing on the raw digital image to identify certain regions of the digital image as being representative of collagen or a specific form of collagen. In other words, the digital image may be masked to identify specific regions as collagen. Different collagen classes may be useful for distinguishing different fibrosis phenotypes. For example, quantitative parameters for fine collagen may be used for distinguishing less severe fibrosis stages (e.g., F0, F1, F2) while quantitative parameters for assembled collagen may be used for distinguishing more severe fibrosis stages (e.g., F2, F3, F4).

The selected parameters database 106*f* corresponds to the set of quantitative parameters from databases 106*b-d* (and optionally 106*e*) that are selected for inclusion in a composite score that quantifies phenotype of fibrosis. An example process for selecting the parameters in database 106*f* from the candidate parameters and calibration data set is described in detail in relation to FIGS. 10-12. Briefly, the selected parameters correspond to those that distinguish between fibrosis phenotypes for a target subject population, that may reflect a specific species, age, race, gender, disease state, any other suitable characteristics, or a combination thereof. Specifically, the selected parameters may be those that, for the digital images in the calibration data set corresponding to the relevant target subject population, are able to distinguish across different fibrosis phenotypes without introducing a large amount of noise.

Generally, the selected parameters stored in the selected parameters database 106*f* may be different for different objectives. For example, a first set of parameters are selected for characterizing disease severity (e.g., to derive a composite score that provides a continuous scale for F0-F4). A second set of parameters may be selected for characterizing progression of fibrosis. A third set of parameters may be selected for characterizing regression of fibrosis in response to treatment, such as a drug. A fourth set of parameters may be selected for classifying the type of fibrosis (e.g., to derive a composite score that provides a continuous scale and is thresholded by a cut-off value to classify the subject as a type of fibrosis, such as NASH 1 versus NASH 2). Any of the parameters selected for the first, second, third, and fourth sets may overlap with one another, but generally, each of the described sets of parameters may include one or more parameters that are unique to that set, or that are not included in every other set. Each set of selected parameters is used to compute a different composite score, with a specific objective. In this manner, for a single digital image of a biological tissue sample, different sets of selected parameters may be applied to derive different composite scores, to reflect multiple objectives (e.g., characterizing the disease severity and type of fibrosis) at the same time.

Moreover, the selected parameters stored in the selected parameters database 106*f* may be specific to a certain set of calibration digital images that share similar metadata, such as patients of a specific population (e.g., age, race, gender, symptoms, blood test data), and different sets of selected parameters may be applicable to different populations.

In one example, as is described in more detail in relation to FIGS. 10-12, to determine whether a particular parameter can distinguish across different fibrosis phenotypes without introducing much noise, the parameter's distribution of values (across the relevant calibration digital images for a specific fibrosis phenotype) is evaluated for its mean and standard deviation, and the mean and standard deviation are evaluated for different fibrosis phenotypes. If the mean value changes for different fibrosis phenotypes, and the standard deviation for the individual phenotypes is not too large, then the parameter is selected. As is described in more detail below, the selected parameters are combined to provide one or more composite scores that quantify the fibrosis phenotype of the human or animal in the digital image. It should be understood that the techniques and examples described in relation to FIGS. 10-12 are shown for illustrative purposes only, other methods of selecting informative parameters from a set of candidate parameters may be used without departing from the scope of the present disclosure.

In an implementation, the user device 108 provides a digital image taken of a histopathology tissue section, to the server 104 over the network 102. The digital image may include a two-dimensional digital image(s), a three-dimensional digital image(s), a digital image stack(s), a static digital image(s), a time-course series of digital images, a digital movie(s), or any suitable combination thereof. The digital image includes an optical marker specific to collagen, either from collagen-specific stains used in histopathology methods, or from intrinsic bio-optical markers specific to collagen (and fibrosis) intrinsic to the optical imaging method (such as second harmonic generation) fibrosis, or in more general terms to any kind of collagen. Unlike the digital images in the calibration data set database 106*a*, the digital image from the user device 108 may not be associated with a known phenotype of fibrosis. Alternatively, the fibrosis phenotype may be known, or already assessed by a pathologist or clinician, but the present disclosure is used to validate that assessed phenotype. Generally, other metadata may accompany the digital image, such as any of the other metadata described in relation to database 106*a*. That metadata may be used to determine which parameters to include in the composite score calculation. For example, the metadata may inform which subset of calibration digital images should be applied, and therefore which selected parameters to use to compute the composite score.

The server 104 performs a computational analysis on the digital image to obtain a score (or scores) that quantify the entire fibrosis phenotype, or a subset of the phenotype. That score can be used to describe the severity, progression, regression, or type of the fibrosis in the tissue sample. To obtain the score(s), the server 104 performs the method 200 described in relation to FIG. 2, which is based on a set of quantitative parameters that are described in relation to FIGS. 3-9, which are selected based on a calibration technique, such as the one described in relation to FIGS. 10-12.

In some implementations, the server 104 computes only a single score that characterizes the fibrosis in the digital image received from the user device 108. Alternatively, the server 104 computes multiple composite scores, each of which characterizes the fibrosis in the digital image. For example, different composite scores may be computed for the same digital image, including one composite score that quantifies the disease severity (e.g., F0-F4), optionally another composite score that quantifies the progression of fibrosis, optionally another composite score that quantifies the regression of fibrosis in response to treatment, and optionally another composite score that quantifies the type of fibrosis (e.g., NASH 1 versus NASH 2). For each composite score calculation, different quantitative parameters are selected to be specific to the objective (e.g., to quantify severity, progression, regression, or type of fibrosis), as is discussed in more detail in relation to FIG. 10.

In some implementations, different composite scores are computed for different levels of features. Specifically, a separate composite score may be computed for tissue level parameters, morphometric level parameters, and texture level parameters, or for any combination of two levels (e.g., tissue and morphometric, morphometric and texture, or tissue and texture). Then, the resulting composite scores may be combined into a single value, or combined as a vector to represent the fibrosis phenotype. In some implementations, using different composite scores for different levels of features is one way to remove potential biases that may be introduced as a result of one level having significantly more selected parameters than another level. Generally, the composite scores may be normalized by the number of selected parameters in a particular group, such as the level.

The server 104 provides the composite score(s) over the network 102 to the user device 108, which may display the composite score(s) or an indication of the composite score(s) to a user. For example, the user device 108 may display the actual number or numbers corresponding to the composite score, which represents the fibrosis phenotype, such as disease severity, progression or regression of fibrosis, or type of fibrosis for the subject associated with the uploaded digital image. Similarly, the server 104 may provide a processed version of the digital image to the user device 108 for display. The processed version of the digital image may indicate specific regions of the digital image that are identified as certain classes of collagen, such as that depicted in FIG. 14, or certain collagen objects, such as that depicted in FIG. 13.

Moreover, the server 104 may save the composite score (s), the original digital image, any metadata associated with the digital image (e.g., patient information such as race, gender, age, blood test data, or image information such as imaging modality, resolution, when the sample or image was taken) and any indication of the extracted features of the digital image to produce the composite score(s) into database 106, or any other suitable database accessible to the server 104. Saved data may further include the parameters calculated from the digital image, and any processed versions of the digital image, such as those that indicate locations of specific collagen objects (FIG. 13) or certain collagen classes (FIG. 14).

FIG. 2 is a flowchart of a method 200 that may be implemented by the system 100 to quantify the phenotype of fibrosis from a histopathological digital image of tissue. In general, the method 200 provides an analysis that precisely quantifies the phenotype of fibrosis in the tissue sample. While the steps of the method 200 are described below as being performed by the server 104, it will be understood that the user device 108 may perform any of all of the steps of the method 200 locally, or any or all of the steps of the method 200 may be performed by some other device, without departing from the scope of the present disclosure.

There are various ways to quantify the phenotype of fibrosis in the tissue sample, without departing from the scope of the present disclosure. One primary purpose of the approach described herein is to reduce the dimension of the data set (e.g., the set of candidate parameters), to identify and select parameters that account for the variance in the calibration digital images (e.g., the variation in the way collagen appears in digital images for different fibrosis phenotypes). The selected parameters may be referred to herein as "principal parameters," which are identified based on the computational methods described herein, to account for the changes in appearance of collagen for different types of fibrosis, different severities of fibrosis, and different stages of progression or regression of fibrosis. The methods described in relation to FIG. 2 are provided as examples only, and it will be understood that other methods may also be used to identify the principal parameters, such as principal component analysis (PCA).

At step 220, the server 104 receives a digital image of a biological tissue sample, wherein the digital image includes a depiction of collagens in the biological tissue sample. The present disclosure is not limited to any specific tissue imaging method, so long as the digital image includes a distinguishing marker specific to one or multiple collagen molecules versus non-collagen molecules. Notably, the systems and methods of the present disclosure may apply the same computational analysis to quantify the fibrosis phenotype of the tissue sample, regardless of the specific tissue type, histology staining method, collagen biomarker, collagen optical biomarker or imaging modality that was used to create the digital image.

Generally, the imaging method to take the digital image of the biological tissue sample involves an optical marker specific to collagen. That optical marker may be from collagen-specific stains used in histopathology methods, from intrinsic bio-optical markers specific to collagens (and fibrosis) intrinsic to the optical imaging method (such as second harmonic generation) fibrosis, or in more general terms to any kind of collagen.

The server 104 performs some pre-processing of the digital image when the digital image is received. Such pre-processing may include identification of the collagens that appear in the digital image, examples of which are depicted in FIGS. 13-14 and 18. For instance, FIG. 13 depicts an example of detection of a collagen object in a digital image, from a set of adjacent pixels that represent an amount of collagen. In another example, FIG. 14 depicts a pre-processed digital image in which different collagen classes are identified, including steatosis, fine collagen, and assembled collagen. FIG. 18 depicts another example of a raw, unprocessed digital image (top row) and the processed version (bottom row), depicting identification of different collagen objects of different types, indicated by gray-scale intensity. For example, such pre-processing may include color-based segmentation, thresholding, filtering, enhancement, texture analysis, binarization, edge detection, region analysis, Fourier transformation, object detection, object analysis segmentation, skeletonization, machine learning, deep learning for image processing, 2D and 3D variants of any of these techniques, and any other computational technique that can enrich the extraction of collagens from an image.

In some implementations, the image is taken using a tissue imaging method or combination of tissue imaging methods or modalities that can enrich the detection signal of the fibrous tissue, so that the collagen in the resulting image of the tissue sample is more easily detected. Suitable tissue imaging methods include fluorescent imaging, using ex-vivo fresh tissue, performing optical biopsies, in-vivo imaging (such as endoscopic imaging, for example). In general, any digital imaging and optical methods may be used, including stained histopathology slides imaged by Whole Slide Imaging Scanners, two-photon microscopy, fluorescence imaging, structured imaging, polarized imaging, Coherent anti-Stokes Raman Scattering (CARS), Optical Coherence Tomography (OCT) images, and other images of biological tissue, or any suitable combination thereof, in any configuration and wavelength. The present disclosure is applicable to any kind of digital imaging methods that would generate a digital image by virtual biopsy imaging, such as is used for fresh tissue imaging and/or endoscopy.

At step 222, the server 104 processes the image received at step 220, to quantify a plurality of parameters, each parameter describing a feature of the collagens in the biological tissue sample that is expected to be different for different phenotypes of fibrosis. The quantitative parameters represent various features of collagens appearing in the digital image, either individually or as a group, and are the same parameters described above, selected from the set of candidate parameters stored in databases 106b-d and described below in detail in relation to FIGS. 3-9. The quantitative parameters are generally sorted into three levels and are described in detail in relation to FIGS. 3-9.

As discussed briefly above, these quantitative parameters can be categorized into at least three distinct levels: (1) the tissue level, in which collagen is measured macroscopically as an aggregation of collagens across the image; (2) the morphometric level, which quantifies the shape and size of individual collagens (or collagen objects); and (3) the texture level, which quantifies the organization of the collagens with respect to one another across the image.

FIGS. 3-9 depict how different types of parameters are used to quantify fibrosis in digital image. Each of FIGS. 3, 5-6, and 8 depicts a set of three exemplary digital images of tissue samples (included in the calibration data set, for example) having different known fibrosis phenotypes (e.g., F0, F2, and F4). The same three digital images are repeated in each of FIGS. 3, 5-6, and 8. Below each image in each of these figures is a table that lists example quantitative parameters that represent tissue level features (FIG. 3), morphometric level features (FIGS. 5-6), or texture level features (FIG. 8) for each fibrosis phenotype of F0, F2, and F4.

Moreover, each of FIGS. 4, 7, and 9 show data structures that summarize the tissue level features (FIG. 4), morphometric level features (FIG. 7), and texture level features (FIG. 9) and indicate whether each parameter is selected to be included in the generation of the composite score. For FIGS. 5-9 (morphometric level and texture level), the quantitative parameters are based on histogram analysis, as is described in detail below. The figures only indicate exemplary quantitative parameters, and are for illustrative purposes only. For simplicity of the figures, not all possible parameters are shown, and it should be understood that different parameters could be used without departing from the scope of the present disclosure. The appendix includes another exemplary list of quantitative parameters that may be used, but different parameters could also be included, such as different metrics and statistics, including those of different cut-off values than indicated.

Moreover, each quantitative parameter described herein may be representative of the collagen as a whole (e.g., total collagen represented in the digital image), or may otherwise only represent a portion of the depicted collagen. For example, the parameters may be computed only on specific area of the tissue (e.g., border, portal region, around glomeruli in the kidney, or any other suitable specific area), in subgroups or classes of the collagen, such as large versus small collagen (as defined by the form factors of their skeleton), faint versus dense collagen (as defined by the average optical/pixel/intensity value), individual versus bundles of collagen fibers, fine versus assembled collagen (see FIG. 14), other suitable classes of collagen, or any suitable combination thereof. Limiting certain quantitative parameters to specific areas or subgroups of the total collagen depicted in the digital image may lead to more precision for quantifying fibrosis phenotype in the final scoring system.

As discussed below, some parameters relate to a single value characterization of the collagen depicted in the digital image (e.g., tissue level parameters). Other parameters (e.g., morphometric level parameters and/or texture level parameters) relate to multiple value characterization, and involve statistics (e.g., computed from histograms) to account for trends (e.g., mean), transition (e.g., statistics limited to above or below cut-off values, or ranges in between cut-off values), or variability (e.g., standard deviation, kurtosis). These examples are provided for illustrative purposes only, and in some implementations, tissue level parameters are associated with histograms and involve statistics. Moreover, in some implementations, morphometric level parameters and/or texture level parameters relate to single value characterization. The cut-off values segment a distribution into multiple sections, so as to create different statistics for the sections. For example, long versus short collagen fibers may be defined by a cut-off value separating long versus short. Similarly, another cut-off value may define low versus high texture entropy. The selection of cut-off values may be performed by a user, and optimized for specific tissues. For example, a low cut-off value for length may be used for rodents, while a higher cut-off value for length may be used for larger animals. As another example, the user may select the cut-off value depending on the phenotyping objective, such as detection of a fibrosis phenotype with low severity (e.g., F0, F1, F2) compared to higher severity (e.g., F2, F3, F4).

At the tissue level (FIGS. 3-4), these features describe the macroscopic properties of the collagens in the digital image and quantify overall amounts of collagen depicted across the entire digital image. Example tissue level parameters include the object normalized count, skeleton nodes normalized count, collagen reticulation index, total collagen area ratio, the large collagen object normalized density (count per area of surface), the small collagen object normalized density, and others. As depicted in FIG. 4, some parameters correspond to transformations of one or more other parameters. For example, total collagen area ratio is one parameter listed in FIG. 4, and so is its square root. Similarly, the assembled/fine CAR ratio is a parameter that corresponds to a transformation of two other parameters: the assembled CAR and fine CAR. These transformations are included as examples only, and in general, any transformation may be applied to any combination of the parameters, including parameters at the tissue, morphometric, and texture levels.

At the morphometric level (FIGS. 5-7), these features describe the morphometric characteristics (or the shape and dimensions) of the collagens in the digital image. Because there is generally more than a single collagen (e.g., one fiber) depicted in the digital image, and in severe cases, that could be many collagens or collagen objects (e.g., multiple fibers, bundles of fibers, or tissue regions) depicted in the image. Rather than including a different value characterizing each individual collagen fiber as a parameter, the approach described herein uses a histogram analysis to analyze the distribution of morphometric values across the collagens or collagen objects appearing in the image. In this manner, the quantitative parameters describing morphometric level features correspond to statistics that can be derived from the histogram (or distribution of values), such as normalized count, mean, median, standard deviation, skew, kurtosis, and any other suitable statistic. Example morphometric characteristics that are used to generate the histograms include length, skeleton length, width, eccentricity, solidity, curvature ration, area, perimeter, collagen density, color intensity, form factors such as area to perimeter ratio, or color to curvature ratio, and any other relevant parameter that describes the shape, dimensions, or appearance of collagens.

At the texture level (FIGS. 8-9), these features describe the organization, or distribution, of the collagens in the digital image. In order to capture how the collagens are distributed throughout the image, the approach described herein uses a histogram analysis, similar to the morphometric level analysis described above in relation to FIGS. 5-7. However, rather than analyzing the distribution of values across collagens or collagen objects (as is done for morphometric level features), the texture level features involve a distribution of values across different regions of the digital image. For example, a sample value may be measured from a sample window (having size smaller than the size of the overall digital image) of the digital image. A set of sample values are derived as the sample window is shifted (in an overlapping or non-overlapping manner) in both dimensions (x- and y-directions) across the digital image. That set of sample values corresponds to a sample distribution for the texture level analysis, which generates a histogram of the sample values for a digital image. In this manner, the quantitative parameters describing texture level features correspond to statistics that can be derived from the histogram (or distribution of values), such as normalized count, mean, medium, standard deviation, skew, kurtosis, and any other suitable statistic. Example texture characteristics that are used to generate the histograms include second order statistics including the collagen image pixel intensity level co-occurrence matrix and subsequent calculation of parameters such as energy, homogeneity, correlation, inertia, entropy, skewness, kurtosis, related GLCM parameters, and any other relevant parameter that describes the organization of collagens in an image.

Returning to FIG. 2, at step 224, the server 104 combines the plurality of parameters quantified at step 222, to obtain one or more composite scores indicative of a phenotype of fibrosis for the biological tissue sample. The composite score may be derived based on a mathematical transfer function that combines some or all of the quantitative parameters computed at step 222, such as a sum of the selected quantitative parameters, where the sum can be a normalized sum or a weighted sum. The composite score precisely quantifies the fibrosis phenotype (generally along a continuous scale so that it improves upon the coarse, categorical approaches of the prior art by providing wide dynamic range and high resolution), and can be used to describe the state of fibrosis in the biological tissue sample, progression of fibrosis in the sample, or regression of fibrosis in the sample in response to treatment. Derivation of the method to compute the composite score may involve manual and/or automated methods that reduce the dimension of the calibration data set (by identifying candidate parameters that have the best signal-to-noise and are validated by existing models of fibrosis (such as METAVIR), as described below with reference to FIGS. 10-12), identify correlations and/or principal components, or any combination thereof.

In general, multiple composite scores may be computed, where each composite score is specific to a particular level (e.g., tissue, morphometric, or texture) and/or collagen class (e.g., fine or assembled). For example, a Tissue-Level Fibrosis Composite Score, a Morphometric-Level Composite Score, a Texture-Level Composite Score, and/or a phenotypic composite score may be calculated. Then, the resulting composite scores may be combined to obtain a single value for quantifying the fibrosis phenotype. Alternatively, the multiple composite scores may remain separate as a vector of a small set of numbers that describe the fibrosis phenotype. The composite score may be referred to herein as the Fibrosis Composite Score.

The following description of FIGS. 10-12 provide ways to select specific parameters from the list of candidate quantifiable parameters, for inclusion in the computation of the composite score.

FIG. 10 depicts an exemplary flow diagram of a calibration process 1000 for selecting parameters to include in a calculation of a composite score for quantifying a phenotype for fibrosis for a specific population. The process 1000 is discussed below as being performed by the server 104, but in general, may be performed locally by the user device 108 or by any other suitable device that can receive the digital image from the user device 108, either over the network 102 otherwise.

As discussed above in relation to the selected parameters database 106f, the calibration process 1000 selects parameters from a set of candidate parameters that are computed based on a set (or a relevant subset) of calibration digital images. The selected parameters are included in the calculation of a composite score that quantifies phenotype of fibrosis, so the selected parameters should distinguish between fibrosis phenotypes for a specific target subject population (e.g., corresponding to the subject of the digital image that is uploaded by the user device 108, for example). Generally, the selected parameters are those that, for the digital images in the calibration data set corresponding to the relevant target subject population, are able to distinguish across different fibrosis phenotypes without introducing a large amount of noise.

At step 1032, the server 104 receives the calibration digital images 1030 (described in relation to the calibration data set database 106*a*), and separates the calibration digital images 1030 according to fibrosis phenotype. As discussed above, the fibrosis phenotypes correspond to fibrosis-related conditions having different outcomes of fibrosis disease. Those different outcomes may correspond to different disease severity (e.g., NASH-CRN F disease stages, which include F0, F1, F2, F3, and F4), different values or ranges of a fibrosis-related biomarker that is indicative of progression of fibrosis, regression of fibrosis in response to treatment, or both, or different classes of fibrosis (e.g., NASH 1 versus NASH 2). For the calibration data set, the fibrosis phenotypes of the digital images are known, and are as evaluated by a physician or pathologist (e.g., F0, F1, F2, F3, F4, NASH 1, NASH 2, etc.). The calibration digital images 1030 are separated into different categories according to their corresponding known fibrosis phenotypes.

The calibration digital images 1030 may be further separated according to other metadata associated with the images 1030. For example, the calibration digital images 1030 may be separated according to specific population data, such as race, gender, age, organ, or any other known data associated with the calibration digital images 1030.

At step 1034, a fibrosis phenotype iterative parameter i is initialized to one. At step 1042, the server 104 receives three sets of candidate parameters (e.g., candidate tissue level parameters 1036, candidate morphometric level parameters 1038, and candidate texture level parameters 1040) are received, and for the i-th fibrosis phenotype, processes the corresponding calibration digital images 1030 to obtain mean and standard deviation of each candidate parameter.

When the digital images are evaluated for the quantitative parameters, all of the image may be processed, or just some of the image may be processed, such as regions of the image corresponding to a specific target location of the biological tissue sample. For example, when the biological tissue sample is of the liver, the collagens in the image may be located in the septal region, the portal region, the perivascular region, the collagen capsule, or structural collagen regions. Any of these regions or a combination thereof may be included for assessment. An understanding of these regions may also inform the selection of candidate parameters. For example, anatomically relevant collagens may include septal bridges in liver or glomeruli in kidney, that have expected sizes, shapes, and arrangements. Moreover, the digital images may be preprocessed to identify certain collagen objects (see FIG. 13) or to identify certain collagen classes (see FIG. 14).

As discussed above, some of the candidate parameters 1036, 1038, and 1040 may correspond to the total collagens in the image, or a subset of the collagens, such as those of a particular collagen class or classes. If the i-th fibrosis phenotype is not the last fibrosis phenotype to be considered (decision block 1044), the iterative parameter i is incremented (step 1046) and the process 1000 returns to block 1042 to evaluate the mean and standard deviation of each candidate parameter for the next fibrosis phenotype. This process is repeated until all fibrosis phenotypes are considered (e.g., the i-th fibrosis phenotype is the last fibrosis phenotype.

In other words, for each fibrosis phenotype i, the corresponding calibration digital images 1030 are identified (having known fibrosis phenotypes corresponding to the i-th fibrosis phenotype). For each of those identified images, the set of candidate parameters across the three levels (1036, 1038, and 1040) are evaluated, to generate an N×M matrix, where N corresponds to the total number of candidate parameters, and M corresponds to the number of calibration digital images for the i-th fibrosis phenotype. For each candidate parameter, the mean and standard deviation of the M corresponding values are evaluated.

When all fibrosis phenotypes have been evaluated for mean and standard deviation, the process 1000 then evaluates the means and standard deviations of each candidate parameter to determine whether the respective candidate parameter has a signal (e.g., distinguishes between different fibrosis phenotypes of the calibration data set) without introducing much noise (e.g., low standard deviation within a given fibrosis phenotype of the calibration data set). To begin, the server 104 proceeds to step 1048 to initialize a candidate parameter j to one.

At step 1050, for the j-th candidate parameter, the server 104 assesses the rate of change of the mean for different fibrosis phenotypes, to determine whether the j-th candidate parameter distinguishes between different fibrosis phenotypes. The rate of change may be assessed across different types of fibrosis so as to determine whether the j-th candidate parameter can distinguish between types, or across different stages of fibrosis progression, so as to determine whether the j-th candidate parameter can distinguish between different severities of fibrosis.

At step 1052, the server 104 determines whether the rate of change evaluated at step 1050 is above a first threshold, to determine whether the j-th candidate parameter distinguishes between fibrosis phenotypes. If so, the server 104 proceeds to step 1054 to determine whether the standard deviation for the j-th candidate parameter is below a second threshold. If so, the server 104 proceeds to step 1056 to add the j-th candidate parameter to a set of selected parameters. Then, if the j-th parameter is not the last candidate parameter (decision block 1058), then the iterative candidate parameter j is incremented (step 1062), and the server 104 returns to block 1050 to consider the next j-th candidate parameter. For any j-th parameter for which the rate of change is below (or equal to) the first threshold (decision block 1052) or the standard deviation is above (or equal to) the second threshold (decision block 1052), the server 104 skips step 1056, does not add the j-th parameter to the set of selected parameters, and proceeds to the next parameter. These steps (1050, 1052, 1054, 1056, 1058, and 1062) are repeated until all M candidate parameters have been considered and are either selected or not selected. At step 1060, the server 104 outputs the set of selected parameters.

FIG. 11 depicts four plots of exemplary mean values of normalized candidate parameters (y-axes) for different fibrosis phenotypes (x-axes, representing fibrosis progression with increasing disease severity). As depicted in FIG. 11, many candidate parameters do not change much for different fibrosis phenotypes, and thus have relatively flat slopes. These candidate parameters with flat slopes (e.g., rate of change around zero) are generally not selected because they do not distinguish between the different fibrosis phenotypes (decision block 1052).

Other candidate parameters exhibit moderate or large rates of changes and have positive, significant slopes. These candidates are more likely to be selected because they correlate in a positive manner with the different fibrosis phenotypes (e.g., they increase with increasing disease severity or fibrosis progression). However, if these candidate parameters are associated with large standard deviations (decision block 1054), in either one or more fibrosis phenotypes, then that candidate parameter is not selected because it would introduce undesirable noise to the composite score calculation that could outweigh the benefit of being able to distinguish between fibrosis phenotypes.

Lastly, still other candidate parameters exhibit negative rates of change and have negative, significant slopes. These candidates are also likely to be selected because even though they correlate in a negative manner with the different fibrosis phenotypes (e.g., they decrease with increasing disease severity or fibrosis progression), they still distinguish between fibrosis phenotypes.

In some embodiments, the present disclosure allows for different parameters to be selected for distinguishing between different sets of fibrosis phenotypes. For example, a first set of parameters may be selected to distinguish between F0 and F2, and a second set of parameters (with potential for overlap with the first set of parameters) may be selected to distinguish between F2 and F4. In this case, the system may take an adaptive approach that generates a first composite score for the first set of parameters, and a second composite score for the second set of parameters, and then align the two composite scores (e.g., by adding an offset to one or both of the scores) so that they have the same value where they meet (i.e., for the F2 phenotype). Similarly, the system may align the derivatives of the two composite scores so that the slopes are the same for the F2 phenotype.

FIG. 12 depicts an exemplary plot showing the noise versus rate of change of various quantitative parameters in a calibration data set for a specific population, according to an illustrative implementation. Specifically, the x-axis of FIG. 12 corresponds to an absolute value of the rate of change of the mean of a candidate parameter across different fibrosis phenotypes of the calibration data set, while the y-axis corresponds to the noise of the candidate parameter (e.g., represented by standard deviation). Each dot corresponds to a different candidate parameter. The vertical line at a rate of change of about 2, corresponds to the first threshold (decision block 1052), and the horizontal line corresponds to the second threshold (decision block 1054). According to the process 1000 of FIG. 10, the candidate parameters corresponding to dots below and to the right of the threshold lines have low signal-to-noise ratios, and are selected for inclusion in computation of the composite score. The other candidate parameters above or to the left of the threshold lines are not selected.

As depicted in FIGS. 10 and 12, at decision blocks 1052 and 1054, the rate of change and standard deviations are simply compared to first and second thresholds, respectively, but in general, more complex calculations may be used. For example, for principal component analysis (PCA), an input matrix may be provided, that includes the parameter values for the set of candidate parameters, for the different known fibrosis phenotypes (e.g., F0-F4). The output of the PCA corresponds to the parameters that account for the variation in collagen features for the different fibrosis phenotypes.

The steps of the process 1000 are depicted in FIG. 10 in a particular order, but it should be understood that the order of any step of the process 1000 is not necessarily dependent on a previous step. For example, any of the steps of process 1000 may be reversed, or performed in parallel with other steps, without departing from the scope of the present disclosure, as long as any steps that depend on other steps are performed subsequent to those steps. Moreover, the process 1000 is described as being performed by the server 104, but any of the steps, including all of them, could be performed locally on the user device 108 or any other suitable device capable of receiving the digital image directly or indirectly from the user device 108.

The present disclosure provides several advantages over known categorical approaches to phenotyping fibrosis. Several advantages are applicable to patients. Specifically, for the patient having a fibrosis-related condition, the present disclosure improves to improve the evaluation and follow up of fibrotic disease conditions such as IPF, Inflammatory Bowel Disease (IBD), Hepatitis (A, B, or C), Chronic Kidney Disease, scleroderma, Macular degeneracies, NASH, Alcoholic Steatosis Hepatitis (ASH), Cirrhosis, Primary Biliary Cholangitis and Primarily Biliary Cirrhosis, renal disease, scarring, Duchenne muscular dystrophy, myocardial infarction and repair, glaucoma uterine, all kinds of manifestation of fibrosis in cancers, among others by providing a robust and accurate way to evaluate both severity of fibrosis and phenotype of fibrosis progression and presenting the patient's fibrosis phenotype in a simple score. The automated systems and methods disclosed herein also avoid inter-pathologist and intra-pathologist evaluation errors, further improving its robustness and accuracy.

Moreover, the scoring systems and methods disclosed herein provide a continuous scale that has a high detection threshold and wide dynamic range to quantify fibrosis phenotype of the biological tissue with sensitivity and precision. Due to its very high signal-to-noise, the present disclosure is sensitive to even slight changes in fibrosis progression in a patient, on shorter time scales than previously allowed with coarse systems. In other words, the scoring systems and methods disclosed herein improve upon earlier fibrosis phenotyping approaches because they do not require waiting for long periods of time before detecting a change in the progression of fibrosis. The robustness of the fibrosis scoring systems and methods disclosed herein also improve the efficiency of development and approval of new therapeutics, by being able to detect small changes in both progression and regression of fibrosis in response to treatment.

The present disclosure also provides scoring systems and methods that are specific to a particular fibrosis phenotype of the patient or expressed in the image of the biological tissue. For example, the scoring systems and methods could distinguish between to pediatric NASH type I versus pediatric NASH type II. Other fibrosis phenotypes may exist, such as T2-diabetes induced NASH versus obesity induced NASH.

Other advantages are applicable to the physician and clinical team that cares for the patients. For example, the present disclosure improves the personalized management of fibrotic disease therapeutic regimens, such as treatments for IPF, Inflammatory Bowel Disease (IBD), Hepatitis (A, B, or C), Chronic Kidney Disease, scleroderma, Macular degeneracies, NASH, Alcoholic Steatosis Hepatitis (ASH), Cirrhosis, Primary Biliary Cholangitis and Primarily Biliary Cirrhosis, renal disease, scarring, Duchenne muscular dystrophy, myocardial infarction and repair, glaucoma uterine, all kinds of manifestation of fibrosis in cancers, among others. By providing a robust, sensitive, accurate and reproducible way to evaluate fibrosis severity and progression in a continuous way, the present disclosure allows improved monitoring of patients over the long run, and even across different clinical teams.

Moreover, while other approaches are sometimes unable to distinguish between even the coarse categorical stages of fibrosis (e.g., such as the intermediate stages of fibrosis, F2 and F3), the present disclosure has no such issue. The present disclosure provides a robust, sensitive, accurate, and reproducible way to evaluate fibrosis, which allows for an improved monitoring of patients during clinical trials. The systems and methods disclosed herein can also be fully automated, meaning that throughput is high, and a pathologist is not needed for scoring. The present disclosure is also fully compatible with existing workflows in the pathology labs, as images can be processed in real time.

The present disclosure may be used to identify biomarkers or other characteristics that correlate with fibrosis, that may not have been otherwise identified. Specifically, the systems and methods of the present disclosure provide an efficient and robust way of analyzing and phenotyping digital images of tissue samples, such as those in the calibration data set described above. If the calibration data set further includes metadata corresponding clinical data, such as blood test data, the present disclosure may be used to identify certain biomarkers in the blood test data (or any other characteristic of the subject, such as age, race, gender) that correlate with the severity, progression, regression, or type of fibrosis. For example, male and female subjects may exhibit fibrosis differently from one another, and may respond to treatment differently. These differences can be assessed and characterized with the systems and methods of the present disclosure.

Other advantages are applicable to pharmaceutical companies that are researching potential therapies to treat fibrosis-related conditions. For example, the present disclosure improves translational research and product launches by gathering comprehensive high quality data related to animal and/or patient reaction to investigational compounds, hence increasing the likelihood of successfully developing new anti-fibrotic drugs, and/or minimize or reduce the fibrosis-related side effects of new or existing drugs. Because the scoring systems and methods can be automated, they are suitable for mid-throughput and even high-throughput workflows, which are more likely to accelerate the discovery of new therapeutic compounds. Moreover, the present disclosure is translational and applies both to pre-clinical models and clinical, across all kinds of fibrotic diseases and oncology (stromae).

The continuous, robust, sensitive, accurate and reproducible scoring methods and systems disclosed herein provide an efficient, quantitative, unbiased, and automated way to evaluate fibrosis during pre-clinical trials (see FIG. 15) and clinical trials (see FIG. 16). The present disclosure reduces the number of animals (or patients) required to obtain statistically relevant data. The systems and methods disclosed herein examine multiple quantitative parameters that describe fibrosis stages, progression, and regression, which can be used to support a detailed understanding of the effect of investigational compounds, and optionally the mechanism of action of those compounds.

As an example of a pre-clinical, discovery application, FIG. 15 depicts on the left, a heat map of a set of selected quantitative parameters (y-axis) describing collagen features in a calibration data set for different populations, including control, untreated, vehicle, and treated at different doses (10, 30, and 100 mg/kg), and on the right, a bar graph showing the fibrosis composite score is able to track the different stages of disease, including response to treatment, according to an illustrative implementation.

As an example of a clinical application, FIG. 16 depicts on top, a heat map of a set of selected quantitative parameters (y-axis) describing collagen features in a calibration data set for different populations, including F0, F1, F2, F3, and F4 (x-axis), and on the bottom, a bar graph showing the fibrosis composite score is able to track the different stages of the disease, according to an illustrative implementation.

In another example of a clinical application, FIG. 19 depicts two heat maps of a set of candidate quantitative parameters (y-axes) describing collagen features in a calibration data set for different NASH 1 and NASH 2 populations, for F0, F1, and F2 patients. For two selected parameters, the fibrosis composite score is able to correctly classify the patients as NASH 1 versus NASH 2 about 85% of the time, according to an illustrative implementation.

Furthermore, because the present disclosure can be specific to the fibrosis phenotype of its patient: for instance pediatric NASH type 1 vs pediatric NASH type 2, or T2-diabetes induced NASH versus obesity induced NASH, the scoring systems and methods can be used to better understand the response of the patient to treatment, or the lack thereof.

Moreover, the present disclosure may be developed into an automatic diagnostic tool for patient, hence accelerating the access to important patient information while reducing the cost of the diagnostic. The scoring systems and methods of the present disclosure are consistent with existing methods of characterizing fibrosis (see FIG. 17), but improves upon those categorical methods by providing a wide dynamic range and fine resolution for quantifying fibrosis. As an example, FIG. 17 depicts data indicating the fibrosis composite score correlates with the Nakanuma fibrosis stages, and provides improved dynamic range relative to the Nakanuma system, according to an illustrative implementation.

While many of the examples in the present disclosure are described with reference to features of collagens in a digital image, the present disclosure may be also applied to detecting and characterizing other features of tissue. For example, NASH tissues tend to include fat vacuoles, and the systems and methods of the present disclosure may be used to characterize tissue features such as fat vacuoles.

The systems and methods of the present disclosure are described as using a calibration data set to select quantitative parameters from a set of candidate parameters. In general, a machine learning technique may be used without departing from the scope of the present disclosure, that analyzes a training data set with user-defined feature classification criteria, to learn the optimal combination of image features that best distinguish between fibrosis phenotypes. For example, artificial intelligence and machine learning techniques may be applied to reduce the dimension of the set of candidate parameters, identify correlations between parameters and fibrosis phenotypes, and identify principal components to establish meaningful composite scores.

It is to be understood that while various illustrative implementations have been described, the forgoing description is merely illustrative and does not limit the scope of the invention. While several examples have been provided in the present disclosure, it should be understood that the disclosed systems, components and methods may be embodied in many other specific forms without departing from the scope of the present disclosure.

The examples disclosed can be implemented in combinations or sub-combinations with one or more other features described herein. A variety of apparatus, systems and methods may be implemented based on the disclosure and still fall within the scope of the invention. Also, the various features described or illustrated above may be combined or integrated in other systems or certain features may be omitted, or not implemented.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

All references cited herein are incorporated by reference in their entirety and made part of this application.

APPENDIX

Example List of Candidate Parameters for Quantifying Fibrosis
- Total Collagen Phenotype Normalized Counts
- Fine Collagen Phenotype Normalized Counts
- Assembled Collagen Phenotype Normalized Counts
- Skeleton Nodes Normalized Count
- Skeleton Branch Normalized Count
- Collagen Reticulation Index
- Collagen STRUCTURE Index
- Total Collagen Area Ratio (%)
- SQRT(Total Collagen Area ratio %)
- Fine Collagen Area Ratio (%)
- SQRT(Fine Collagen Area Ratio)
- Assembled Collagen Area Ratio (%)
- Collagen Fiber Density %
- SQRT(Assembled/Fine CAR)
- Assembled/
- Fine CAR Ratio
- Normalized count of Short for Length at 30 Cut Off for All Collagen phenotypes
- Normalized count of Long for Length at 30 Cut Off for All Collagen phenotypes
- mean for Length at 30 Cut Off for All Collagen phenotypes
- median for Length at 30 Cut Off for All Collagen phenotypes
- std for Length at 30 Cut Off for All Collagen phenotypes
- skew for Length at 30 Cut Off for All Collagen phenotypes
- kurtosis for Length at 30 Cut Off for All Collagen phenotypes
- Normalized count of Short for Total Skeleton Length at 27 Cut Off for All Collagen phenotypes
- Normalized count of Long for Total Skeleton Length at 27 Cut Off for All Collagen phenotypes
- mean for Total Skeleton Length at 27 Cut Off for All Collagen phenotypes
- median for Total Skeleton Length at 27 Cut Off for All Collagen phenotypes
- std for Total Skeleton Length at 27 Cut Off for All Collagen phenotypes
- skew for Total Skeleton Length at 27 Cut Off for All Collagen phenotypes
- kurtosis for Total Skeleton Length at 27 Cut Off for All Collagen phenotypes
- Normalized count of Thin for Width at 5 Cut Off for All Collagen phenotypes
- Normalized count of Thick for Width at 5 Cut Off for All Collagen phenotypes
- mean for Width at 5 Cut Off for All Collagen phenotypes
- median for Width at 5 Cut Off for All Collagen phenotypes
- std for Width at 5 Cut Off for All Collagen phenotypes
- skew for Width at 5 Cut Off for All Collagen phenotypes
- kurtosis for Width at 5 Cut Off for All Collagen phenotypes
- Normalized count of Short for Perimeter at 100 Cut Off for All Collagen phenotypes
- Normalized count of Long for Perimeter at 100 Cut Off for All Collagen phenotypes
- mean for Perimeter at 100 Cut Off for All Collagen phenotypes
- median for Perimeter at 100 Cut Off for All Collagen phenotypes
- std for Perimeter at 100 Cut Off for All Collagen phenotypes
- skew for Perimeter at 100 Cut Off for All Collagen phenotypes
- kurtosis for Perimeter at 100 Cut Off for All Collagen phenotypes
- Normalized count of Small for Area at 240 Cut Off for All Collagen phenotypes
- Normalized count of Large for Area at 240 Cut Off for All Collagen phenotypes
- mean for Area at 240 Cut Off for All Collagen phenotypes
- median for Area at 240 Cut Off for All Collagen phenotypes
- std for Area at 240 Cut Off for All Collagen phenotypes
- skew for Area at 240 Cut Off for All Collagen phenotypes
- kurtosis for Area at 240 Cut Off for All Collagen phenotypes
- Normalized count of Small for Filled Area at 250 Cut Off for All Collagen phenotypes
- Normalized count of Large for Filled Area at 250 Cut Off for All Collagen phenotypes
- mean for Filled Area at 250 Cut Off for All Collagen phenotypes
- median for Filled Area at 250 Cut Off for All Collagen phenotypes
- std for Filled Area at 250 Cut Off for All Collagen phenotypes
- skew for Filled Area at 250 Cut Off for All Collagen phenotypes
- kurtosis for Filled Area at 250 Cut Off for All Collagen phenotypes
- Normalized count of Faint for Density at 0.18 Cut Off for All Collagen phenotypes
- Normalized count of Dense for Density at 0.18 Cut Off for All Collagen phenotypes
- mean for Density at 0.18 Cut Off for All Collagen phenotypes
- median for Density at 0.18 Cut Off for All Collagen phenotypes
- std for Density at 0.18 Cut Off for All Collagen phenotypes
- skew for Density at 0.18 Cut Off for All Collagen phenotypes
- kurtosis for Density at 0.18 Cut Off for All Collagen phenotypes
- Normalized count of Low for Area to Perimeter Ratio at 2.8 Cut Off for All Collagen phenotypes
- Normalized count of High for Area to Perimeter Ratio at 2.8 Cut Off for All Collagen phenotypes mean for Area to Perimeter Ratio at 2.8 Cut Off for All Collagen phenotypes
median for Area to Perimeter Ratio at 2.8 Cut Off for All Collagen phenotypes
std for Area to Perimeter Ratio at 2.8 Cut Off for All Collagen phenotypes
skew for Area to Perimeter Ratio at 2.8 Cut Off for All Collagen phenotypes
kurtosis for Area to Perimeter Ratio at 2.8 Cut Off for All Collagen phenotypes
Normalized count of Linear for Tortuosity at 1.1 Cut Off for All Collagen phenotypes
Normalized count of Tortuous for Tortuosity at 1.1 Cut Off for All Collagen phenotypes
mean for Tortuosity at 1.1 Cut Off for All Collagen phenotypes
median for Tortuosity at 1.1 Cut Off for All Collagen phenotypes
std for Tortuosity at 1.1 Cut Off for All Collagen phenotypes
skew for Tortuosity at 1.1 Cut Off for All Collagen phenotypes
kurtosis for Tortuosity at 1.1 Cut Off for All Collagen phenotypes
Normalized count of Rounded for Eccentricity at 0.8 Cut Off for All Collagen phenotypes
Normalized count of Elongated for Eccentricity at 0.8 Cut Off for All Collagen phenotypes
mean for Eccentricity at 0.8 Cut Off for All Collagen phenotypes
median for Eccentricity at 0.8 Cut Off for All Collagen phenotypes
std for Eccentricity at 0.8 Cut Off for All Collagen phenotypes
skew for Eccentricity at 0.8 Cut Off for All Collagen phenotypes
kurtosis for Eccentricity at 0.8 Cut Off for All Collagen phenotypes
Normalized count of Porous for Solidity at 0.3 Cut Off for All Collagen phenotypes
Normalized count of Compact for Solidity at 0.3 Cut Off for All Collagen phenotypes
mean for Solidity at 0.3 Cut Off for All Collagen phenotypes
median for Solidity at 0.3 Cut Off for All Collagen phenotypes
std for Solidity at 0.3 Cut Off for All Collagen phenotypes
skew for Solidity at 0.3 Cut Off for All Collagen phenotypes
kurtosis for Solidity at 0.3 Cut Off for All Collagen phenotypes
Normalized count of Horizontal for Orientation at 45 Cut Off for All Collagen phenotypes
Normalized count of Vertical for Orientation at 45 Cut Off for All Collagen phenotypes
mean for Orientation at 45 Cut Off for All Collagen phenotypes
median for Orientation at 45 Cut Off for All Collagen phenotypes
std for Orientation at 45 Cut Off for All Collagen phenotypes
skew for Orientation at 45 Cut Off for All Collagen phenotypes
kurtosis for Orientation at 45 Cut Off for All Collagen phenotypes
Normalized count of Dull for Skew at 3 Cut Off for All Fibrosis Texture
Normalized count of Sharp for Skew at 3 Cut Off for All Fibrosis Texture
mean for Skew at 3 Cut Off for All Fibrosis Texture
median for Skew at 3 Cut Off for All Fibrosis Texture
std for Skew at 3 Cut Off for All Fibrosis Texture
skew for Skew at 3 Cut Off for All Fibrosis Texture
kurtosis for Skew at 3 Cut Off for All Fibrosis Texture
Normalized count of Foggy for Kurtosis at 25 Cut Off for All Fibrosis Texture
Normalized count of Crisp for Kurtosis at 25 Cut Off for All Fibrosis Texture
mean for Kurtosis at 25 Cut Off for All Fibrosis Texture
median for Kurtosis at 25 Cut Off for All Fibrosis Texture
std for Kurtosis at 25 Cut Off for All Fibrosis Texture
skew for Kurtosis at 25 Cut Off for All Fibrosis Texture
kurtosis for Kurtosis at 25 Cut Off for All Fibrosis Texture
Normalized count of Blurry for Energy at 0.18 Cut Off for All Fibrosis Texture
Normalized count of Resolved for Energy at 0.18 Cut Off for All Fibrosis Texture
mean for Energy at 0.18 Cut Off for All Fibrosis Texture
median for Energy at 0.18 Cut Off for All Fibrosis Texture
std for Energy at 0.18 Cut Off for All Fibrosis Texture
skew for Energy at 0.18 Cut Off for All Fibrosis Texture
kurtosis for Energy at 0.18 Cut Off for All Fibrosis Texture
Normalized count of Homogeneous for Homogeneity at 0.35 Cut Off for All Fibrosis Texture
Normalized count of Organized for Homogeneity at 0.35 Cut Off for All Fibrosis Texture
mean for Homogeneity at 0.35 Cut Off for All Fibrosis Texture
median for Homogeneity at 0.35 Cut Off for All Fibrosis Texture
std for Homogeneity at 0.35 Cut Off for All Fibrosis Texture
skew for Homogeneity at 0.35 Cut Off for All Fibrosis Texture
kurtosis for Homogeneity at 0.35 Cut Off for All Fibrosis Texture
Normalized count of Irregular for Correlation at 0.35 Cut Off for All Fibrosis Texture
Normalized count of Patterned for Correlation at 0.35 Cut Off for All Fibrosis Texture
mean for Correlation at 0.35 Cut Off for All Fibrosis Texture
median for Correlation at 0.35 Cut Off for All Fibrosis Texture
std for Correlation at 0.35 Cut Off for All Fibrosis Texture
skew for Correlation at 0.35 Cut Off for All Fibrosis Texture
kurtosis for Correlation at 0.35 Cut Off for All Fibrosis Texture
Normalized count of Uniform for Inertia at 30 Cut Off for All Fibrosis Texture
Normalized count of Contrasted for Inertia at 30 Cut Off for All Fibrosis Texture
mean for Inertia at 30 Cut Off for All Fibrosis Texture
median for Inertia at 30 Cut Off for All Fibrosis Texture
std for Inertia at 30 Cut Off for All Fibrosis Texture
skew for Inertia at 30 Cut Off for All Fibrosis Texture
kurtosis for Inertia at 30 Cut Off for All Fibrosis Texture
Normalized count of Smooth for Entropy at 3.5 Cut Off for All Fibrosis Texture
Normalized count of Rough for Entropy at 3.5 Cut Off for All Fibrosis Texture
mean for Entropy at 3.5 Cut Off for All Fibrosis Texture median for Entropy at 3.5 Cut Off for All Fibrosis Texture
std for Entropy at 3.5 Cut Off for All Fibrosis Texture
skew for Entropy at 3.5 Cut Off for All Fibrosis Texture
kurtosis for Entropy at 3.5 Cut Off for All Fibrosis Texture
Normalized count of Short for Length at 30 Cut Off for Fine Collagen phenotypes
Normalized count of Long for Length at 30 Cut Off for Fine Collagen phenotypes
mean for Length at 30 Cut Off for Fine Collagen phenotypes
median for Length at 30 Cut Off for Fine Collagen phenotypes
std for Length at 30 Cut Off for Fine Collagen phenotypes
skew for Length at 30 Cut Off for Fine Collagen phenotypes
kurtosis for Length at 30 Cut Off for Fine Collagen phenotypes
Normalized count of Short for Total Skeleton Length at 27 Cut Off for Fine Collagen phenotypes
Normalized count of Long for Total Skeleton Length at 27 Cut Off for Fine Collagen phenotypes
mean for Total Skeleton Length at 27 Cut Off for Fine Collagen phenotypes
median for Total Skeleton Length at 27 Cut Off for Fine Collagen phenotypes
std for Total Skeleton Length at 27 Cut Off for Fine Collagen phenotypes
skew for Total Skeleton Length at 27 Cut Off for Fine Collagen phenotypes
kurtosis for Total Skeleton Length at 27 Cut Off for Fine Collagen phenotypes
Normalized count of Thin for Width at 5 Cut Off for Fine Collagen phenotypes
Normalized count of Thick for Width at 5 Cut Off for Fine Collagen phenotypes
mean for Width at 5 Cut Off for Fine Collagen phenotypes
median for Width at 5 Cut Off for Fine Collagen phenotypes
std for Width at 5 Cut Off for Fine Collagen phenotypes
skew for Width at 5 Cut Off for Fine Collagen phenotypes
kurtosis for Width at 5 Cut Off for Fine Collagen phenotypes
Normalized count of Short for Perimeter at 100 Cut Off for Fine Collagen phenotypes
Normalized count of Long for Perimeter at 100 Cut Off for Fine Collagen phenotypes
mean for Perimeter at 100 Cut Off for Fine Collagen phenotypes
median for Perimeter at 100 Cut Off for Fine Collagen phenotypes
std for Perimeter at 100 Cut Off for Fine Collagen phenotypes
skew for Perimeter at 100 Cut Off for Fine Collagen phenotypes
kurtosis for Perimeter at 100 Cut Off for Fine Collagen phenotypes
Normalized count of Small for Area at 240 Cut Off for Fine Collagen phenotypes
Normalized count of Large for Area at 240 Cut Off for Fine Collagen phenotypes
mean for Area at 240 Cut Off for Fine Collagen phenotypes
median for Area at 240 Cut Off for Fine Collagen phenotypes
std for Area at 240 Cut Off for Fine Collagen phenotypes
skew for Area at 240 Cut Off for Fine Collagen phenotypes
kurtosis for Area at 240 Cut Off for Fine Collagen phenotypes
Normalized count of Small for Filled Area at 250 Cut Off for Fine Collagen phenotypes
Normalized count of Large for Filled Area at 250 Cut Off for Fine Collagen phenotypes
mean for Filled Area at 250 Cut Off for Fine Collagen phenotypes
median for Filled Area at 250 Cut Off for Fine Collagen phenotypes
std for Filled Area at 250 Cut Off for Fine Collagen phenotypes
skew for Filled Area at 250 Cut Off for Fine Collagen phenotypes
kurtosis for Filled Area at 250 Cut Off for Fine Collagen phenotypes
Normalized count of Faint for Density at 0.18 Cut Off for Fine Collagen phenotypes
Normalized count of Dense for Density at 0.18 Cut Off for Fine Collagen phenotypes
mean for Density at 0.18 Cut Off for Fine Collagen phenotypes
median for Density at 0.18 Cut Off for Fine Collagen phenotypes
std for Density at 0.18 Cut Off for Fine Collagen phenotypes
skew for Density at 0.18 Cut Off for Fine Collagen phenotypes
kurtosis for Density at 0.18 Cut Off for Fine Collagen phenotypes
Normalized count of Low for Area to Perimeter Ratio at 2.8 Cut Off for Fine Collagen phenotypes
Normalized count of High for Area to Perimeter Ratio at 2.8 Cut Off for Fine Collagen phenotypes
mean for Area to Perimeter Ratio at 2.8 Cut Off for Fine Collagen phenotypes
median for Area to Perimeter Ratio at 2.8 Cut Off for Fine Collagen phenotypes
std for Area to Perimeter Ratio at 2.8 Cut Off for Fine Collagen phenotypes
skew for Area to Perimeter Ratio at 2.8 Cut Off for Fine Collagen phenotypes
kurtosis for Area to Perimeter Ratio at 2.8 Cut Off for Fine Collagen phenotypes
Normalized count of Linear for Tortuosity at 1.1 Cut Off for Fine Collagen phenotypes
Normalized count of Tortuous for Tortuosity at 1.1 Cut Off for Fine Collagen phenotypes
mean for Tortuosity at 1.1 Cut Off for Fine Collagen phenotypes
median for Tortuosity at 1.1 Cut Off for Fine Collagen phenotypes
std for Tortuosity at 1.1 Cut Off for Fine Collagen phenotypes
skew for Tortuosity at 1.1 Cut Off for Fine Collagen phenotypes
kurtosis for Tortuosity at 1.1 Cut Off for Fine Collagen phenotypes
Normalized count of Rounded for Eccentricity at 0.8 Cut Off for Fine Collagen phenotypes
Normalized count of Elongated for Eccentricity at 0.8 Cut Off for Fine Collagen phenotypes
mean for Eccentricity at 0.8 Cut Off for Fine Collagen phenotypes
median for Eccentricity at 0.8 Cut Off for Fine Collagen phenotypes std for Eccentricity at 0.8 Cut Off for Fine Collagen phenotypes skew for Eccentricity at 0.8 Cut Off for Fine Collagen phenotypes kurtosis for Eccentricity at 0.8 Cut Off for Fine Collagen phenotypes Normalized count of Porous for Solidity at 0.3 Cut Off for Fine Collagen phenotypes Normalized count of Compact for Solidity at 0.3 Cut Off for Fine Collagen phenotypes mean for Solidity at 0.3 Cut Off for Fine Collagen phenotypes median for Solidity at 0.3 Cut Off for Fine Collagen phenotypes std for Solidity at 0.3 Cut Off for Fine Collagen phenotypes skew for Solidity at 0.3 Cut Off for Fine Collagen phenotypes kurtosis for Solidity at 0.3 Cut Off for Fine Collagen phenotypes Normalized count of Horizontal for Orientation at 45 Cut Off for Fine Collagen phenotypes Normalized count of Vertical for Orientation at 45 Cut Off for Fine Collagen phenotypes mean for Orientation at 45 Cut Off for Fine Collagen phenotypes median for Orientation at 45 Cut Off for Fine Collagen phenotypes std for Orientation at 45 Cut Off for Fine Collagen phenotypes skew for Orientation at 45 Cut Off for Fine Collagen phenotypes kurtosis for Orientation at 45 Cut Off for Fine Collagen phenotypes Normalized count of Short for Length at 30 Cut Off For Assembled Collagen phenotypes Normalized count of Long for Length at 30 Cut Off For Assembled Collagen phenotypes mean for Length at 30 Cut Off For Assembled Collagen phenotypes median for Length at 30 Cut Off For Assembled Collagen phenotypes std for Length at 30 Cut Off For Assembled Collagen phenotypes skew for Length at 30 Cut Off For Assembled Collagen phenotypes kurtosis for Length at 30 Cut Off For Assembled Collagen phenotypes Normalized count of Short for Total Skeleton Length at 27 Cut Off For Assembled Collagen phenotypes Normalized count of Long for Total Skeleton Length at 27 Cut Off For Assembled Collagen phenotypes mean for Total Skeleton Length at 27 Cut Off For Assembled Collagen phenotypes median for Total Skeleton Length at 27 Cut Off For Assembled Collagen phenotypes std for Total Skeleton Length at 27 Cut Off For Assembled Collagen phenotypes skew for Total Skeleton Length at 27 Cut Off For Assembled Collagen phenotypes kurtosis for Total Skeleton Length at 27 Cut Off For Assembled Collagen phenotypes Normalized count of Thin for Width at 5 Cut Off For Assembled Collagen phenotypes Normalized count of Thick for Width at 5 Cut Off For Assembled Collagen phenotypes mean for Width at 5 Cut Off For Assembled Collagen phenotypes median for Width at 5 Cut Off For Assembled Collagen phenotypes std for Width at 5 Cut Off For Assembled Collagen phenotypes skew for Width at 5 Cut Off For Assembled Collagen phenotypes kurtosis for Width at 5 Cut Off For Assembled Collagen phenotypes Normalized count of Short for Perimeter at 100 Cut Off For Assembled Collagen phenotypes Normalized count of Long for Perimeter at 100 Cut Off For Assembled Collagen phenotypes mean for Perimeter at 100 Cut Off For Assembled Collagen phenotypes median for Perimeter at 100 Cut Off For Assembled Collagen phenotypes std for Perimeter at 100 Cut Off For Assembled Collagen phenotypes skew for Perimeter at 100 Cut Off For Assembled Collagen phenotypes kurtosis for Perimeter at 100 Cut Off For Assembled Collagen phenotypes Normalized count of Small for Area at 240 Cut Off For Assembled Collagen phenotypes Normalized count of Large for Area at 240 Cut Off For Assembled Collagen phenotypes mean for Area at 240 Cut Off For Assembled Collagen phenotypes median for Area at 240 Cut Off For Assembled Collagen phenotypes std for Area at 240 Cut Off For Assembled Collagen phenotypes skew for Area at 240 Cut Off For Assembled Collagen phenotypes kurtosis for Area at 240 Cut Off For Assembled Collagen phenotypes Normalized count of Small for Filled Area at 250 Cut Off For Assembled Collagen phenotypes Normalized count of Large for Filled Area at 250 Cut Off For Assembled Collagen phenotypes mean for Filled Area at 250 Cut Off For Assembled Collagen phenotypes median for Filled Area at 250 Cut Off For Assembled Collagen phenotypes std for Filled Area at 250 Cut Off For Assembled Collagen phenotypes skew for Filled Area at 250 Cut Off For Assembled Collagen phenotypes kurtosis for Filled Area at 250 Cut Off For Assembled Collagen phenotypes Normalized count of Faint for Density at 0.18 Cut Off For Assembled Collagen phenotypes Normalized count of Dense for Density at 0.18 Cut Off For Assembled Collagen phenotypes mean for Density at 0.18 Cut Off For Assembled Collagen phenotypes median for Density at 0.18 Cut Off For Assembled Collagen phenotypes std for Density at 0.18 Cut Off For Assembled Collagen phenotypes skew for Density at 0.18 Cut Off For Assembled Collagen phenotypes kurtosis for Density at 0.18 Cut Off For Assembled Collagen phenotypes Normalized count of Low for Area to Perimeter Ratio at 2.8 Cut Off For Assembled Collagen phenotypes
Normalized count of High for Area to Perimeter Ratio at 2.8 Cut Off For Assembled Collagen phenotypes
mean for Area to Perimeter Ratio at 2.8 Cut Off For Assembled Collagen phenotypes
median for Area to Perimeter Ratio at 2.8 Cut Off For Assembled Collagen phenotypes
std for Area to Perimeter Ratio at 2.8 Cut Off For Assembled Collagen phenotypes
skew for Area to Perimeter Ratio at 2.8 Cut Off For Assembled Collagen phenotypes
kurtosis for Area to Perimeter Ratio at 2.8 Cut Off For Assembled Collagen phenotypes
Normalized count of Linear for Tortuosity at 1.1 Cut Off For Assembled Collagen phenotypes
Normalized count of Tortuous for Tortuosity at 1.1 Cut Off For Assembled Collagen phenotypes
mean for Tortuosity at 1.1 Cut Off For Assembled Collagen phenotypes
median for Tortuosity at 1.1 Cut Off For Assembled Collagen phenotypes
std for Tortuosity at 1.1 Cut Off For Assembled Collagen phenotypes
skew for Tortuosity at 1.1 Cut Off For Assembled Collagen phenotypes
kurtosis for Tortuosity at 1.1 Cut Off For Assembled Collagen phenotypes
Normalized count of Rounded for Eccentricity at 0.8 Cut Off For Assembled Collagen phenotypes
Normalized count of Elongated for Eccentricity at 0.8 Cut Off For Assembled Collagen phenotypes
mean for Eccentricity at 0.8 Cut Off For Assembled Collagen phenotypes
median for Eccentricity at 0.8 Cut Off For Assembled Collagen phenotypes
std for Eccentricity at 0.8 Cut Off For Assembled Collagen phenotypes
skew for Eccentricity at 0.8 Cut Off For Assembled Collagen phenotypes
kurtosis for Eccentricity at 0.8 Cut Off For Assembled Collagen phenotypes
Normalized count of Porous for Solidity at 0.3 Cut Off For Assembled Collagen phenotypes
Normalized count of Compact for Solidity at 0.3 Cut Off For Assembled Collagen phenotypes
mean for Solidity at 0.3 Cut Off For Assembled Collagen phenotypes
median for Solidity at 0.3 Cut Off For Assembled Collagen phenotypes
std for Solidity at 0.3 Cut Off For Assembled Collagen phenotypes
skew for Solidity at 0.3 Cut Off For Assembled Collagen phenotypes
kurtosis for Solidity at 0.3 Cut Off For Assembled Collagen phenotypes
Normalized count of Horizontal for Orientation at 45 Cut Off For Assembled Collagen phenotypes
Normalized count of Vertical for Orientation at 45 Cut Off For Assembled Collagen phenotypes
mean for Orientation at 45 Cut Off For Assembled Collagen phenotypes
median for Orientation at 45 Cut Off For Assembled Collagen phenotypes
std for Orientation at 45 Cut Off For Assembled Collagen phenotypes
skew for Orientation at 45 Cut Off For Assembled Collagen phenotypes
kurtosis for Orientation at 45 Cut Off For Assembled Collagen phenotypes
Normalized count of Dull for Skew at 1.25 Cut Off for All Tissue Texture Normalized count of Sharp for Skew at 1.25 Cut Off for All Tissue Texture
mean for Skew at 1.25 Cut Off for All Tissue Texture
median for Skew at 1.25 Cut Off for All Tissue Texture
std for Skew at 1.25 Cut Off for All Tissue Texture
skew for Skew at 1.25 Cut Off for All Tissue Texture
kurtosis for Skew at 1.25 Cut Off for All Tissue Texture
Normalized count of Foggy for Kurtosis at 2.5 Cut Off for All Tissue Texture
Normalized count of Crisp for Kurtosis at 2.5 Cut Off for All Tissue Texture
mean for Kurtosis at 2.5 Cut Off for All Tissue Texture
median for Kurtosis at 2.5 Cut Off for All Tissue Texture
std for Kurtosis at 2.5 Cut Off for All Tissue Texture
skew for Kurtosis at 2.5 Cut Off for All Tissue Texture
kurtosis for Kurtosis at 2.5 Cut Off for All Tissue Texture
Normalized count of Blurry for Energy at 0.15 Cut Off for All Tissue Texture
Normalized count of Resolved for Energy at 0.15 Cut Off for All Tissue Texture
mean for Energy at 0.15 Cut Off for All Tissue Texture
median for Energy at 0.15 Cut Off for All Tissue Texture
std for Energy at 0.15 Cut Off for All Tissue Texture
skew for Energy at 0.15 Cut Off for All Tissue Texture
kurtosis for Energy at 0.15 Cut Off for All Tissue Texture
Normalized count of Homogeneous for Homogeneity at 0.05 Cut Off for All Tissue Texture
Normalized count of Organized for Homogeneity at 0.05 Cut Off for All Tissue Texture
mean for Homogeneity at 0.05 Cut Off for All Tissue Texture
median for Homogeneity at 0.05 Cut Off for All Tissue Texture
std for Homogeneity at 0.05 Cut Off for All Tissue Texture
skew for Homogeneity at 0.05 Cut Off for All Tissue Texture
kurtosis for Homogeneity at 0.05 Cut Off for All Tissue Texture
Normalized count of Irregular for Correlation at 0.1 Cut Off for All Tissue Texture
Normalized count of Patterned for Correlation at 0.1 Cut Off for All Tissue Texture
mean for Correlation at 0.1 Cut Off for All Tissue Texture
median for Correlation at 0.1 Cut Off for All Tissue Texture
std for Correlation at 0.1 Cut Off for All Tissue Texture
skew for Correlation at 0.1 Cut Off for All Tissue Texture
kurtosis for Correlation at 0.1 Cut Off for All Tissue Texture
Normalized count of Uniform for Inertia at 300 Cut Off for All Tissue Texture
Normalized count of Contrasted for Inertia at 300 Cut Off for All Tissue Texture
mean for Inertia at 300 Cut Off for All Tissue Texture
median for Inertia at 300 Cut Off for All Tissue Texture
std for Inertia at 300 Cut Off for All Tissue Texture
skew for Inertia at 300 Cut Off for All Tissue Texture
kurtosis for Inertia at 300 Cut Off for All Tissue Texture
Normalized count of Smooth for Entropy at 3.5 Cut Off for All Tissue Texture
Normalized count of Rough for Entropy at 3.5 Cut Off for All Tissue Texture mean for Entropy at 3.5 Cut Off for All Tissue Texture
median for Entropy at 3.5 Cut Off for All Tissue Texture
std for Entropy at 3.5 Cut Off for All Tissue Texture
skew for Entropy at 3.5 Cut Off for All Tissue Texture
kurtosis for Entropy at 3.5 Cut Off for All Tissue Texture

The invention claimed is:

1. A method of computer aided phenotyping of fibrosis-related conditions, the method comprising:
    (a) receiving a digital image of a biological tissue sample, wherein the digital image indicates presence of collagens in the biological tissue sample;
    (b) processing the image to quantify a plurality of parameters, each parameter describing a feature of the collagens in the biological tissue sample that is expected to be different for different phenotypes of fibrosis,
        wherein at least some of the features are selected from at least two of the group consisting of: (1) tissue level features that describe macroscopic characteristics of the collagens depicted in the digital image of the biological tissue sample; (2) morphometric level features that describe morphometric characteristics of the collagens depicted in the digital image of the biological tissue sample; and (3) texture level features that describe an organization of the collagens depicted in the digital image of the biological tissue sample, and
        wherein at least some of the plurality of parameters are statistics associated with histograms corresponding to distributions of the associated parameters across at least some of the digital image; and
    (c) combining at least some of the plurality of parameters in (b) to obtain one or more composite scores that quantify a phenotype of fibrosis for the biological tissue sample.

2. The method of claim 1, wherein at least one of the features in (b) is a tissue level feature, at least another feature in the features of (b) is a morphometric level feature, and at least another feature in the features in (b) is a texture level feature.

3. The method of claim 1, wherein the method is compatible with any modality of imaging that distinguishes between a presence and absence of collagens in the biological tissue sample.

4. The method of claim 3, wherein the method is compatible with at least stained histopathology slides, two photon microscopy, fluorescence imaging, structured imaging, polarized imaging, Coherent anti-Stokes Raman Scattering (CARS), Optical Coherence Tomography (OCT) images, fresh tissue imaging, and endoscopy.

5. The method of claim 1, wherein the depiction of collagens in the biological tissue sample results from an optical marker that is specific to any form of collagen.

6. The method of claim 5, wherein the optical marker is a collagen-specific stain used in a histopathology method.

7. The method of claim 5, wherein the optical marker is an intrinsic bio-optical marker specific to one or more collagens that is intrinsic to an optical imaging method.

8. The method of claim 1, wherein pixels of the digital image indicate presence and quantity of collagens in corresponding volumes of the biological tissue sample.

9. The method of claim 1, wherein at least some of the parameters describing a morphometric level feature or a texture level feature is one of the statistics associated with histograms that result from processing the histograms.

10. The method of claim 9, wherein cut-off values split the histograms into subsets of sample values, and at least some of the statistics are for a single subset of sample values.

11. The method of claim 1, wherein quantifying at least some of the plurality of parameters associated with histograms comprises processing the histograms to identify multiple modes of the histograms that are identified by deconvoluting the histogram.

12. The method of claim 11, wherein some modes of the histograms correspond to phenotypic signatures of the fibrosis-related conditions, wherein deconvoluting the histogram comprises filtering the histogram to determine whether the histogram exhibits a phenotypic signature and to quantify the exhibited phenotypic signature.

13. The method of claim 1, further comprising processing the digital image to distinguish between collagens in the biological tissue sample represented in the digital image.

14. The method of claim 13, wherein each of the plurality of parameters used to obtain at least one of the one or more composite scores in (c) corresponds to one class of collagen.

15. The method of claim 14, wherein the collagen classes distinguish different stages of fibrosis.

16. The method of claim 13, wherein collagen classes include one or more of fine collagen, assembled collagen, and tissue regions.

17. The method of claim 16, wherein each of the plurality of parameters used to obtain the at least one of the one or more composite scores in (c) corresponds to one collagen class.

18. The method of claim 1, wherein different features are selected to quantify different phenotypes of fibrosis.

19. The method of claim 1, wherein the plurality of parameters that are combined in (c) are selected from a list of candidate parameters using a calibration technique involving a calibration data set of calibration digital images taken from biological samples having known phenotypes of fibrosis.

20. The method of claim 1, wherein the method quantifies the severity of fibrosis of the biological tissue sample, progression of fibrosis for the subject, regression of fibrosis for the subject in response to a therapy, or type of fibrosis, on a continuous scale.

21. The method of claim 1, wherein the parameters that describe texture level features include at least one statistical parameter describing the distribution of one or more properties of the collagen image pixel intensity grey level co-occurrence matrix (GLCM) defined on a spatial dimension across the collagen image, the GLCM properties including at least one of the group consisting of: energy, homogeneity, contrast, correlation, inertia, entropy, skewness, and kurtosis.

22. The method of claim 21, wherein the texture level parameters are obtained by an image processing method configured to quantify perceived texture of a collagen image.

23. The method of claim 22, wherein the plurality of parameters that are combined in (c) are selected using artificial intelligence and machine learning.

24. The method of claim 1, wherein the plurality of parameters that are combined in (c) are selected from a set of candidate parameters to reduce the dimension of the set of candidate parameters.

25. The method of claim 1, wherein the image is received from a combination of tissue imaging methods that enrich the detection signal of the fibrous tissue.

26. The claim 25 wherein the imaging methods comprise stained histopathology slides, two photon microscopy, fluorescence imaging, structured imaging, polarized imaging, Coherent anti-Stokes Raman Scattering (CARS), Optical Coherence Tomography (OCT) images, fresh tissue imaging, and endoscopy.

27. A method of computer aided phenotyping of fibrosis-related conditions, the method comprising:
  (a) receiving a digital image of a biological tissue sample, wherein the digital image indicates presence of collagens in the biological tissue sample;
  (b) processing the image to quantify one or more parameters, each parameter describing a feature of the collagens in the biological tissue sample that is expected to be different for different phenotypes of fibrosis,
    wherein at least some of the features are selected from at least two of the group consisting of: (1) tissue level features that describe macroscopic characteristics of the collagens depicted in the digital image of the biological tissue sample; (2) morphometric level features that describe morphometric characteristics of the collagens depicted in the digital image of the biological tissue sample; and (3) texture level features that describe an organization of the collagens depicted in the digital image of the biological tissue sample, and
    wherein one or more of the parameters are statistics associated with histograms corresponding to
  (c) selecting one or combining more distributions of the associated parameters across at least some of the digital image; and than one of the parameters in (b) to obtain one or more composite scores that quantify a phenotype of fibrosis for the biological tissue sample.

* * * * *